US010111455B2

(12) United States Patent
Denis et al.

(10) Patent No.: US 10,111,455 B2
(45) Date of Patent: Oct. 30, 2018

(54) METHODS AND COMPOSITIONS FOR PROCESSING DIETARY FIBERS

(71) Applicant: COSUCRA GROUPE WARCOING S.A., Warcoing (BE)

(72) Inventors: Robin Denis, Erquennes (BE); Alain Durieux, Brussels (BE); Christian Fougnies, Péruwelz (BE)

(73) Assignee: Cosuera Groupe Warcoing S.A., Warcoing (BE)

( * ) Notice: Subject to any disclaimer, the term of this patent is extended or adjusted under 35 U.S.C. 154(b) by 0 days.

(21) Appl. No.: 15/313,564

(22) PCT Filed: Jun. 24, 2015

(86) PCT No.: PCT/EP2015/064215
§ 371 (c)(1),
(2) Date: Nov. 23, 2016

(87) PCT Pub. No.: WO2015/197670
PCT Pub. Date: Dec. 30, 2015

(65) Prior Publication Data
US 2017/0188609 A1    Jul. 6, 2017

(30) Foreign Application Priority Data

Jun. 24, 2014 (EP) .................................. 14173660
Aug. 4, 2014 (BE) ................................ 2014/0598

(51) Int. Cl.
C12P 19/12     (2006.01)
A23L 5/20      (2016.01)
C08B 37/00     (2006.01)
C12P 19/04     (2006.01)
C08L 5/00      (2006.01)
C12R 1/85      (2006.01)
C12N 1/16      (2006.01)
A23L 33/21     (2016.01)

(52) U.S. Cl.
CPC ................ *A23L 5/28* (2016.08); *A23L 33/21* (2016.08); *C08B 37/0051* (2013.01); *C08B 37/0054* (2013.01); *C08L 5/00* (2013.01); *C12N 1/16* (2013.01); *C12P 19/04* (2013.01); *C12R 1/85* (2013.01)

(58) Field of Classification Search
None
See application file for complete search history.

(56) References Cited

U.S. PATENT DOCUMENTS

2008/0255249 A1   10/2008   Hellwege et al.
2010/0143534 A1    6/2010   Brinker et al.

FOREIGN PATENT DOCUMENTS

WO    2006108697 A1    10/2006
WO    2008133512 A1    11/2008

OTHER PUBLICATIONS

PCT International Search Report and Written Opinion dated Sep. 15, 2015 for PCT International Patent Application No. PCT/EP2015/064215, 11 pages.
Yoon S-H et al., entitled "Specificity of yeast (*Saccharomyces cerevisiae*) in removing carbohydrates by fermentation," Carbohydrate Research, vol. 338, No. 10, May 1, 2003, 1127-1132.
Rouwenhorst R J et al., entitled "Localization of inulinase and invertase in *Kluyveromyces* species," Appl. Environ. Microbiol., vol. 56, No. 11, Jan. 1, 1990, 3329-3336.
Nilsson U et al., entitled "Cereal fructans: Hydrolysis by yeast invertase, in vitro and during fermentation," Journal of Cereal Science, vol. 6, No. 1, Jul. 1, 1987, 53-60.
Apolinário A C et al., entitled "Inulin-type fructans: A review on different aspects of biochemical and pharmaceutical technology," Carbohydrate Polymers, vol. 101, Jan. 2014, 368-378.
Receipt in the Case of an Original Deposit Issued Pursuant to Rule 7.1 by BCCM/MUCL, Belgian Coordinated Collections of Microgranisms (BCCM), Mycothèque de l'Universite Catholique de Louvain (MUCL), Accession No. BCCM MUCL 55125, Date of Deposit Oct. 22, 2013, 2 pages.

*Primary Examiner* — Hope Robinson
(74) *Attorney, Agent, or Firm* — Amster, Rothstein & Ebenstein LLP

(57) ABSTRACT

The present invention relates to a method for processing a composition comprising fructan and sucrose, comprising the step of incubating a composition comprising fructan and sucrose, preferably inulin and sucrose, with at least one yeast selected from the group consisting of *Saccharomyces*, and *Kluyveromyces*. Incubation with these yeasts results in the breakdown of free sugars such that purified fructan compositions are obtained.

15 Claims, 21 Drawing Sheets

METHODS AND COMPOSITIONS FOR PROCESSING DIETARY FIBERS

CROSS-REFERENCE TO RELATED APPLICATIONS

This application is a U.S. national stage entry under 35 U.S.C. § 371 of PCT International Patent Application No. PCT/EP2015/064215, filed Jun. 24, 2015, which claims priority to European Patent Application No. 14173660.3, filed Jun. 24, 2014 and Belgian Patent Application No. 2014/0598, filed Aug. 4, 2014, the contents of which are incorporated herein by reference in their entirety.

FIELD OF THE INVENTION

The present invention relates to methods and compositions for processing dietary fibers. In particular, the present invention relates to purification methods of fructan-containing compositions by means of incubating such compositions with yeast to effect free sugars degradation and elimination.

BACKGROUND OF THE INVENTION

Dietary fibers are edible carbohydrates, which are neither digested nor absorbed in the human small intestine and which have been obtained from food material by physical, enzymatic or chemical means and which have a beneficial physiological effect. In general, dietary fibers pass through much of the digestive system intact and may be totally or partially fermented by the intestinal microbiota.

Dietary fibers may be water soluble or water insoluble. Among the water soluble dietary fibers are fructans. Fructans essentially are polymers composed of fructose residues, ending or not with a glucose unit at what would otherwise be the reducing end. The linkage position of the fructose residues determines the type of the fructan. Linkage normally occurs at one of the two primary hydroxyls (OH-1 or OH-6), and there are two basic types of simple fructan: Inulin (the fructosyl residues are linked by β-2,1-linkages) and Levan (the fructosyl residues are linked by β-2,6-linkages). Fructans can be found in many plants as well as microorganisms, where they are stored as a form of energy. For instance inulin is produced in particularly high quantities in chicory roots.

Industrial production of inulin from for instance chicory root typically involves extraction by hot water. This method produces an extract rich in inulin. However free sugars (for instance glucose, fructose and sucrose) are also co-extracted. An inulin rich extract typically contains about 70-85 wt % inulin and 5-13 wt % free sugars, along with 10-17 wt % of other impurities (e.g. salts, proteins, etc.) based on dry matter. The exact composition of for instance chicory inulin rich extracts however varies and for instance depends on the growing conditions, harvest date, variety of chicory, etc.

The method for purifying the inulin rich extract typically contains several steps, including for instance solid/liquid separation, ion exchange, activated carbon filtration, etc. in which the majority of impurities are removed, and inulin rich composition is obtained. However, free sugars which have a structure and/or chemical characteristics very similar to that of fibers such as fructans, in particular inulin, most often are not eliminated from the inulin rich composition, and these can represent between 6 and 16% of the dry matter (based on dry matter for instance 1-2 wt % glucose, 1.5-7 wt % fructose, and 3.5-7 wt % sucrose in inulin rich compositions from chicory roots).

Although physico-chemically and structurally similar to fibers, such as fructans, these free sugars are however distinguished by their nutritional properties, in view of their digestibility which thus provides a high caloric value as opposed to fibers. High free sugars impurities in dietary fiber compositions therefore pose a problem for instance for diabetics. From this point of view, it is highly advisable to minimize the contents of such free sugars, in the inulin rich composition. Moreover, from a technical point of view, often the industrially produced fibers are provided to customers in the form of syrups or powders. In the latter case the last step of the process may involve spray drying. The effectiveness of this well-known technique decreases as the content of free sugars increases, the latter being more "difficult to dry" because of their relative hygroscopicity (mainly fructose), such that increasing the elimination of free sugars, and in particular fructose, prior to drying not only has nutritional, but also technical advantages.

There are several ways of separating free sugars from the fiber extracts, for example fractional precipitation based on the relative solubility or chromatography. However, these physicochemical separation techniques are very expensive and have a limited scale performance. The fractional precipitation technique is used industrially for the production of fibers that contain reduced free sugars amounts. This technique is based on the differential solubility of carbohydrates molecules of different molecular weights. The industrial scale chromatography allows separation of free sugars on different ranges of fiber types and the efficiency is higher than in the case of fractional precipitation, but remains low. In any case it is not possible to separate the free sugars without conceding to a loss of fibers.

In view of the above, there is still a need to develop alternative or improved methods for eliminating free sugars from dietary fiber compositions, in particular fructan compositions, such as inulin compositions. It is accordingly one of the objects of the present invention to overcome or ameliorate at least one of the disadvantages of the prior art, or to provide a useful alternative.

SUMMARY OF THE INVENTION

The present inventors have surprisingly found that the efficiency, yield, cost effectiveness, and/or speed of fructan processing or purification can be markedly improved by incubating a composition comprising fructan and sucrose, preferably inulin and sucrose, with one or more yeast species, in particular yeast species selected from the group comprising or consisting or consisting essentially of *Saccharomyces* and *Kluyveromyces*. It has been found that these yeasts allow for fast removal, elimination, reduction, or fermentation of free sugars (in particular of glucose, fructose and sucrose) from a composition comprising fructan and sucrose, preferably inulin and sucrose, with higher specificity to free sugars relative to fructan, preferably inulin. As a consequence, the efficiency of fructan purification, preferably inulin purification, is increased and the final yield of fructan, preferably inulin, is increased compared to processing of a composition comprising fructan and sucrose without these one or more yeasts. As such, the present method reduces fructan losses, preferably inulin losses, during processing, such as purification, of such composition comprising fructan and sucrose, such as chicory extracts. According to the methods as described herein, processing or (purification) of composition comprising fructan and sucrose, preferably inulin and sucrose, leads to at least 10% reduced free sugars concentrations as compared to compositions comprising fructan and sucrose which have not been processed according to the methods of the present invention. In some embodiments, the composition at the end of the process can be for example free of sucrose. A particular advantageous balance between on the one hand the specificity of the disclosed yeast species for removing, reducing, eliminating, and/or fermenting free sugars, in particular sucrose, but also fructose and glucose, versus an unwanted degradation of fructan, preferably inulin, and on the other hand the speed of removing, reducing, eliminating, and/or fermenting free sugars has been observed by the present inventors.

The present invention in an aspect thus relates to a method for processing, purifying, treating and/or storing a composition comprising fructan and sucrose, preferably inulin and sucrose, comprising incubating a yeast selected from the group comprising or consisting or consisting essentially of *Saccharomyces* and *Kluyveromyces* to such composition. In a further aspect, the present invention relates to a method for removing, eliminating, reducing, and/or fermenting free sugars (in particular of glucose, fructose and sucrose) from a composition comprising fructan and sucrose, preferably inulin and sucrose, comprising the step of incubating such composition with a yeast selected from the group comprising or consisting of *Saccharomyces* and *Kluyveromyces*.

Preferably, the present invention relates to a method for processing a composition comprising fructan and sucrose, comprising the steps of (a) providing a composition comprising fructan and sucrose, wherein said composition comprising fructan and sucrose comprises at least 30% by weight (wt %) of fructan based on the total dry matter weight of said composition; and (b) incubating said composition comprising fructan and sucrose with at least one yeast selected from the group consisting of *Saccharomyces* and *Kluyveromyces*; until a reduction of at least 10% of the initial weight of sucrose in said composition is obtained.

The present invention also encompasses a composition comprising fructan, sucrose and at least one yeast selected from the group consisting of *Saccharomyces bayanus*, *Saccharomyces cerevisiae*, *Kluyveromyces lactis*, and *Saccharomyces boulardii*, wherein said composition comprises at least 30% by weight (wt %) of fructan based on the total dry matter weight of said composition.

The present invention also encompasses a yeast deposited in the Belgian Co-ordinated Collections of Micro-Organisms (BCCM; Université catholique de Louvain, Mycothèque de l'Université catholique de Louvain (MUCL), Croix du Sud 2, box L7.05.06, 1348 Louvain-la-Neuve, Belgium) with accession number MUCL 55125; deposited on Oct. 22, 2013; Depositor: Cosucra groupe Warcoing, rue de la Sucrerie 1, 7740 Warcoing, Belgium.

The present invention also encompasses the use of a yeast selected from the group consisting of *Saccharomyces* and *Kluyveromyces* for reducing the amount of sucrose in a composition comprising sucrose and at least 30% by weight (wt %) of fructan based on the total dry matter weight of said composition.

The independent and dependent claims set out particular and preferred features of the invention. Features from the dependent claims may be combined with features of the independent or other dependent claims as appropriate. The appended claims are also explicitly included in the description.

The above and other characteristics, features and advantages of the present invention will become apparent from the following detailed descriptions, taken in conjunction with the accompanying drawings, which illustrate, by way of examples, the principles of the invention. The reference figures quoted below refer to the attached drawings.

DETAILED DESCRIPTION OF THE INVENTION

Figure 1:
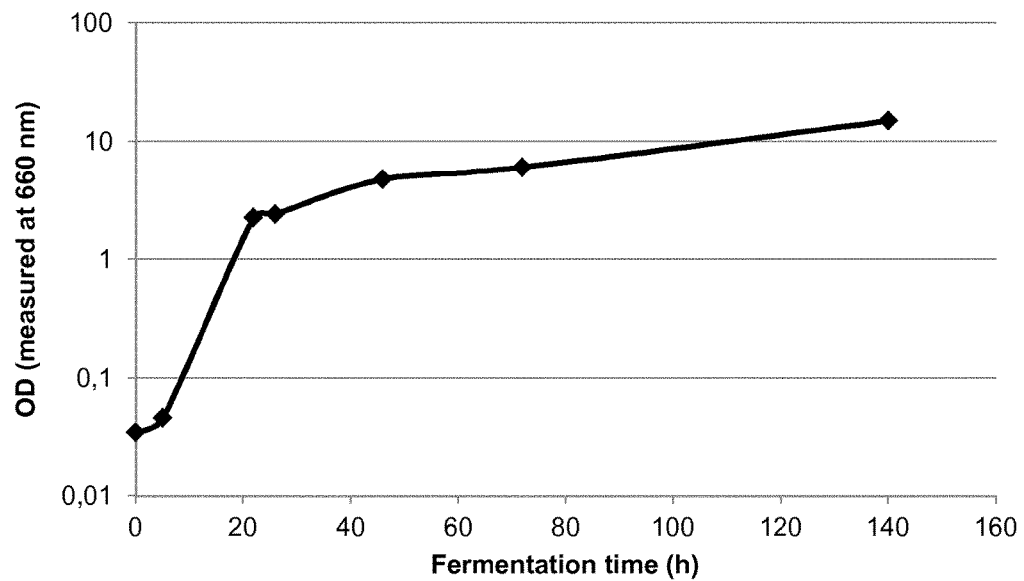
FIG. 1: represents a graph plotting the growth (measured as optical density at 660 nm) over time at 30° C. of *Saccharomyces cerevisiae* w-34/70 incubated with composition B1.
Figure 2:
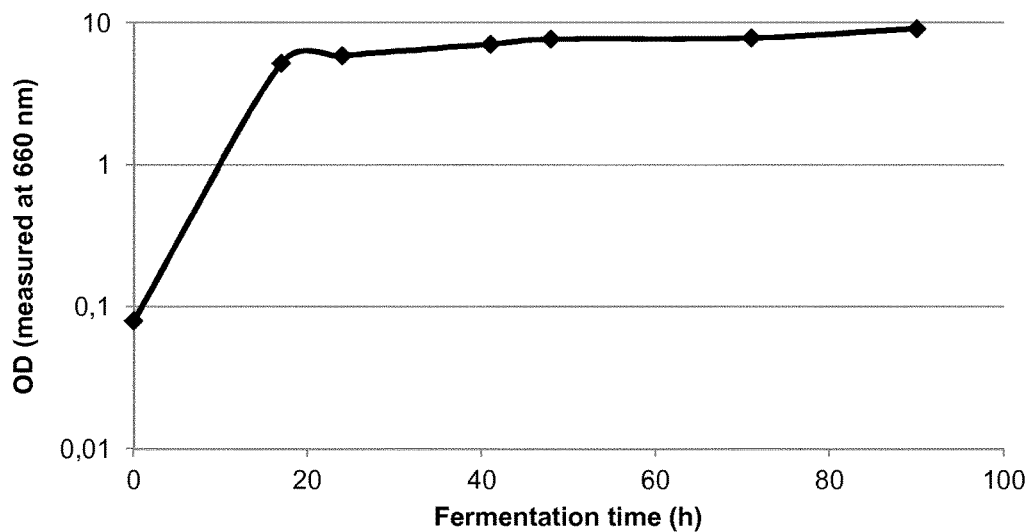
FIG. 2: represents a graph plotting the growth (measured as optical density at 660 nm) over time at 30° C. of *Kluyveromyces lactis* CBS 2103 incubated with composition B2.
Figure 3:
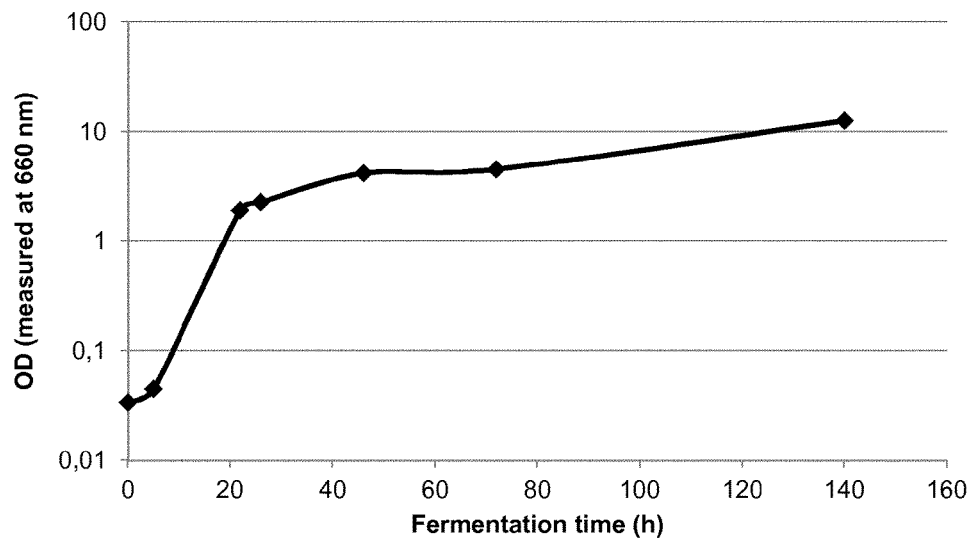
FIG. 3: represents a graph plotting the growth (measured as optical density at 660 nm) over time at 30° C. of *Saccharomyces bayanus* var. *bayanus* MUCL 31495 incubated with composition B3.
Figure 4:
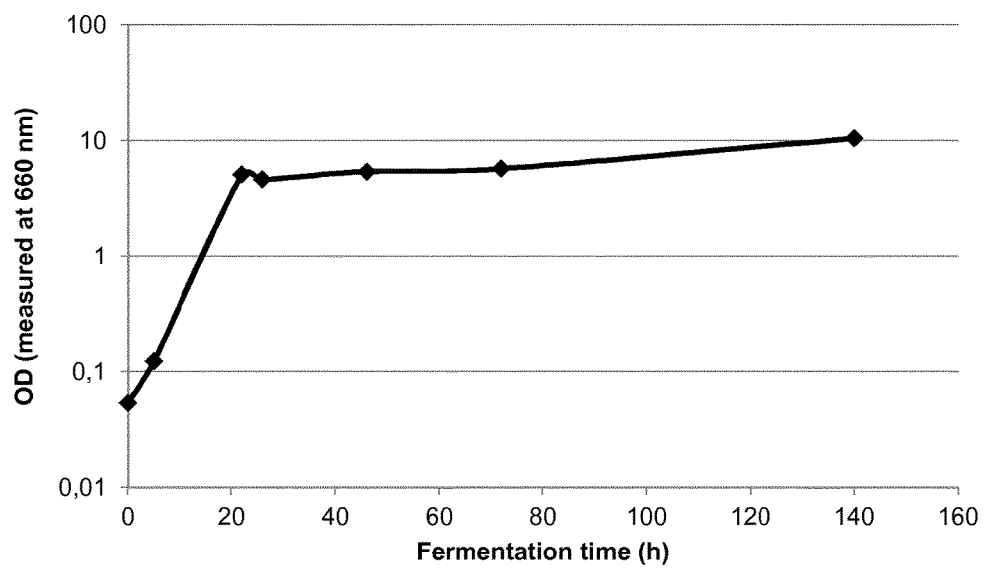
FIG. 4: represents a graph plotting the growth (measured as optical density at 660 nm) over time at 30° C. of *Saccharomyces bayanus* var. *uvarum* MUCL 31491 incubated with composition B4.

Before the present methods of the invention are described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered aspects and embodiments 1 to 74, with any other statement and/or embodiments.

1. A method for processing a composition comprising fructan and sucrose, comprising the steps of (a) providing a composition comprising fructan and sucrose, wherein said composition comprising fructan and sucrose comprises at least 30% by weight (wt %) of fructan based on the total dry matter weight of said composition; and (b) incubating said composition comprising fructan and sucrose with at least one yeast selected from the group consisting of

*Saccharomyces* and *Kluyveromyces*; until a reduction of at least 10% of the initial weight of sucrose in said composition is obtained.
2. The method according to statement 1, wherein said at least one yeast is selected from the group consisting of *Saccharomyces bayanus, Kluyveromyces lactis, Saccharomyces cerevisiae* and *Saccharomyces boulardii*, preferably selected from the group consisting of *Saccharomyces bayanus*, and *Kluyveromyces lactis*, more preferably *Saccharomyces bayanus*.
3. The method according to any one of statements 1 or 2, wherein said composition comprising fructan and sucrose, at the start of the incubation, further comprises one or more free sugars (other than sucrose), preferably wherein said free sugars are selected from the group comprising glucose and fructose.
4. The method according to any one of statements 1 to 3, wherein said composition comprising fructan and sucrose, at the start of the incubation, further comprises one or more free sugars selected from the group comprising, consisting or consisting essentially of glucose and fructose.
5. The method according to any one of statements 1 to 4, wherein said composition comprising fructan and sucrose, at the start of the incubation, comprises at least 1 wt % free sugars based on the total dry matter weight of the composition.
6. The method according to any one of statements 1 to 5, wherein said composition comprising fructan and sucrose, at the start of the incubation, comprises at most 70 wt % free sugars based on the total dry matter weight of the composition.
7. The method according to any one of statements 1 to 6, wherein said fructan has an average degree of polymerization (DP) by number of at least 3, for example of at least 5, for example of at least 7, for example of at least 10, for example at least 15, for example at least 20, for example at least 25, for example at least 70.
8. The method according to any one of statements 1 to 7, wherein said fructan has an average DP by number ranging from 3 to 30.
9. The method according to any one of statements 1 to 8, wherein said fructan is of plant origin, preferably of chicory origin.
10. The method according to any one of statements 1 to 9, wherein said fructan is chicory fructan.
11. The method according to any one of statements 1 to 10, wherein said fructan is inulin, preferably chicory inulin.
12. The method according to any one of statements 1 to 11, wherein said fructan is inulin having a DP ranging from 2 to about 100.
13. The method according to any one of statements 1 to 12, wherein said fructan is inulin having a formulae $GF_n$ and/or $F_m$, wherein G represents a glucose unit, F represents a fructose unit, n is an integer representing the number of fructose units linked to the terminal glucose unit, and m is an integer representing the number of fructose units linked to each other in the carbohydrate chain, wherein n is at least 2, and m is at least 2.
14. The method according to any one of statements 1 to 13, wherein said fructan is partially hydrolyzed.
15. The method according to any one of statements 1 to 14, wherein said fructan comprises or consists or consists essentially of fructo-oligosaccharides.
16. The method according to any one of statements 1 to 15, wherein said fructan comprises or consists or consists essentially of fructo-oligosaccharides, and wherein said fructo-oligosaccharides have an average DP by number of at least 3 and at most 7.
17. The method according to any one of statements 1 to 16, wherein said composition comprising fructan and sucrose comprises at least 40 wt % of fructan based on the total dry matter weight of the composition, preferably at least 50 wt %, even more preferably at least 60 wt %.
18. The method according to any one of statements 1 to 17, wherein said composition comprising fructan and sucrose comprises at most 99 wt % of fructan based on the total dry matter weight of the composition.
19. The method according to any one of statements 1 to 18, wherein said composition comprising fructan and sucrose comprises at least 30 wt % and at most 99 wt % of fructan based on the total dry matter weight of the composition, preferably at least 40 wt %, preferably at least 50 wt %, even more preferably at least 60 wt %.
20. The method according to any one of statements 1 to 19, wherein said composition comprising fructan and sucrose is a liquid composition, preferably an aqueous composition.
21. The method according to any one of statements 1 to 20, wherein said composition comprising fructan and sucrose comprises at least 5 wt % of dry matter based on the total weight of the composition, preferably at least 8 wt %, preferably at least 10 wt %.
22. The method according to any one of statements 1 to 21, wherein said composition comprising fructan and sucrose comprises at least 5 wt % and at most 80 wt % of dry matter based on the total weight of the composition, for example at least 8 wt %, preferably at least 10 wt %, preferably at most 70 wt %, preferably at most 60 wt %, preferably at most 55 wt %, preferably at most 50 wt %.
23. The method according to any one of statements 1 to 22, wherein said composition comprising fructan and sucrose comprises at most 80 wt % of dry matter based on the total weight of the composition, preferably at most 70 wt %, preferably at most 60 wt %, preferably at most 55 wt %, preferably at most 50 wt %.
24. The method according to any one of statements 1 to 23, further comprising the step of adding a nitrogen source to said composition comprising fructan and sucrose, prior and/or during step (b), preferably adding yeast extract.
25. The method according to any one of statements 1 to 24, further comprising one or both of the steps of aerating and agitating the composition comprising fructan and sucrose during the incubation with said yeast.
26. The method according to any one of statements 1 to 25, wherein said composition comprising fructan and sucrose is incubated with said yeast at a temperature of at least the freezing point of the composition, preferably above the freezing point of said composition.
27. The method according to any one of statements 1 to 26, wherein said composition comprising fructan and sucrose is incubated with said yeast at a temperature of at least −5° C., preferably at least 0° C., for example at least 5° C., for example at least 10° C., for example at least 15° C., for example at least 20° C.
28. The method according to any one of statements 1 to 27, wherein said composition comprising fructan and sucrose is incubated with said yeast at a temperature of at most 40° C., for example at most 35° C., for example at most 30° C.
29. The method according to any one of statements 1 to 28, wherein said composition comprising fructan and sucrose is incubated with said yeast at a temperature of at least the freezing point of said composition and at most 40° C., for example of at least −5° C. and at most 40° C., for example at least 0° C. and at most 35° C., for example at least 5° C. and at most 33° C., for example at least 10° C. and at most 30° C., for example at least 15° C. and at most 30° C., for example at least 20° C. and at most 30° C.

30. The method according to any one of statements 1 to 29, wherein said composition comprising fructan and sucrose is incubated with said yeast until a reduction of at least 20% of the initial weight of free sugars in said composition is obtained, preferably a reduction of at least 30%, for example at least 40%, for example at least 50%; preferably at least 60%, for example at least 70%, for example at least 80%, preferably at least 90%, preferably at least 95%, for example at least 98%, for example a reduction of at least 99%.

31. The method according to any one of statements 1 to 30, wherein said composition comprising fructan and sucrose is incubated with said yeast for at least 5 hours, preferably for at least 10 hours.

32. The method according to any one of statements 1 to 31, wherein said composition comprising fructan and sucrose is incubated with said yeast for at most 12 months.

33. The method according to any one of statements 1 to 32, wherein said composition comprising fructan and sucrose is incubated with said yeast at a pH of at least 2.5, preferably a pH of at least 3.0, preferably a pH of at least 3.5.

34. The method according to any one of statements 1 to 33, wherein said composition comprising fructan and sucrose is incubated with said yeast at a pH of at most 8.5, for example at a pH of at most 8.0, for example at a pH of at most 7.5, for example at a pH of at most 7.0

35. The method according to any one of statements 1 to 34, comprising incubating at the start of said incubation at least $10^3$ colony forming units (CFU) per ml, for example at least $10^4$ CFU of said yeast per ml of said composition comprising fructan and sucrose.

36. The method according to any one of statements 1 to 35, comprising incubating at the start of said incubation at most $10^{10}$ CFU/ml, for example at most $10^9$ CFU/ml, for example at most $10^8$ CFU of said yeast per ml of said composition comprising fructan and sucrose.

37. The method according to any one of statements 1 to 36, wherein said composition comprising fructan and sucrose, at the start of the incubation, comprises at least 1 wt % and at most 70 wt % of free sugars including said sucrose based on the total dry matter weight of the composition.

38. The method according to any one of statements 1 to 37, wherein the composition of step (a) is obtained by hot water extraction of a fructan comprising material.

39. The method according to statement 38, wherein said fructan comprising material is from plant origin.

40. The method according to statement 38 or 39, wherein said fructan comprising material is chicory.

41. The method according to any one of statements 1 to 40, wherein the composition of step (a) is obtained using a method comprising the steps of (i) hot water extraction of a fructan comprising material, and (ii) filtration of the hot water extract thereby recovering a composition comprising fructan and sucrose of step (a).

42. The method according to any one of statements 1 to 41, wherein the composition of step (a) is obtained using a method comprising the steps of (i) hot water extraction of a fructan comprising material, (ii) filtration of the hot water extract; and (iii) demineralization of the filtrate of step (ii) thereby recovering a composition comprising fructan and sucrose of step (a).

43. The method according to any one of statements 1 to 42, wherein the composition of step (a) is obtained using a method comprising the steps of (i) hot water extraction of a fructan comprising material, (ii) filtration of the hot water extract; (iii) demineralization of the filtrate of step (ii); and (iv) active carbon filtration of the filtrate of step (iii) thereby recovering a composition comprising fructan and sucrose of step (a).

44. The method according to any one of statements 1 to 43, further comprising the step of removing said yeast after incubation with said composition comprising fructan and sucrose.

45. The method according to any one of statements 1 to 44, wherein said yeast is a lysate of said yeast or an extract of said yeast.

46. The method according to any one of statements 1 to 45, wherein the weight ratio of free sugars including sucrose to fructan in said composition comprising fructan and sucrose at the start of incubation is at least 1:100.

47. The method according to any one of statements 1 to 46, wherein the weight ratio of free sugars including sucrose to fructan in said composition comprising fructan and sucrose at the start of incubation is at most 2.3:1.

48. The method according to any one of statements 1 to 47, wherein the weight ratio of free sugars including sucrose to fructan in said composition comprising fructan and sucrose at the start of incubation is at least 1:100 and at most 2.3:1

49. The method according to any one of statements 1 to 48, wherein the *Saccharomyces* is *Saccharomyces bayanus* var. *uvarum* deposited in the Belgian Co-ordinated Collections of Micro-Organisms (BCCM) with accession number MUCL 55125.

50. The method according to any one of statements 1 to 49, wherein at the end of said incubation step the fructan weight of said composition comprising fructan and sucrose is at most 20% lower than the initial fructan weight at the start of said incubation, preferably at most 10%, most preferably at most 5%.

51. The method according to any one of statements 1 to 50, wherein said composition comprising fructan and sucrose is incubated with said yeast until a reduction of at least 20% of the initial weight of free sugars (including sucrose) in said composition is obtained, preferably a reduction of at least 30%, for example at least 40%, for example at least 50%, for example at least 60%; preferably at least 70%, for example at least 80%, for example at least 90%, preferably at least 95%, for example at least 98%, for example at least 99%, and the fructan weight of said composition comprising fructan and sucrose is at most 20% lower than the initial fructan weight at the start of said incubation, preferably at most 10%, most preferably at most 5%.

52. The method according to any one of statements 1 to 51, wherein said composition comprising fructan and sucrose is incubated with said yeast until a reduction of at least 50% of the initial weight of free sugars (including sucrose) in said composition is obtained preferably a reduction of at least 60%, for example at least 70%, for example at least 80%, preferably at least 90%, preferably at least 95%, for example at least 98%, for example at least 99%, and the fructan weight of said composition comprising fructan is at most 5% lower than the initial fructan weight at the start of said incubation.

53. The method according to any one of statements 1 to 52, wherein said at least one yeast is selected from the group comprising or consisting of *Saccharomyces* and *Kluyveromyces*; preferably said at least one yeast is selected from the group comprising or consisting of *Saccharomyces bayanus, Saccharomyces cerevisiae, Kluyveromyces lactis*, and *Saccharomyces boulardii*; yet more preferably said at least one yeast is selected from the group comprising or consisting of *Saccharomyces bayanus* var. *uvarum, Saccharomyces bayanus* var. *bayanus, Saccharomyces cerevisiae, Saccharomyces boulardii*, and *Kluyveromyces lactis* var. *drosophylarum*, yet more preferably said at least one yeast is selected from the group comprising or consisting of *Saccharomyces bayanus* var. *uvarum* MUCL 55125 (deposited in BCCM/MUCL Louvain-La-Neuve); *Saccharomyces bayanus* MUCL 31491 (obtained from BCCM/MUCL Louvain-La-Neuve), *Saccharomyces bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group), *Kluyveromyces lactis* var. *drosophylarum* CBS 2103 (obtained from CBS-KNAW fungal biodiversity center, Utrecht NL), *Saccharomyces cerevisiae* w-34/70 (obtained from Fermentis, Lesaffre group), and *Saccharomyces boulardii* (obtained from Enterol®; biocodex gamma).

54. The method according to any one of statements 1 to 53, wherein said at least one yeast is selected from the group comprising or consisting of *Saccharomyces*; preferably said at least one yeast is selected from the group comprising or consisting of *Saccharomyces bayanus, Saccharomyces cerevisiae* and *Saccharomyces boulardii*; more preferably *Saccharomyces bayanus* and *Saccharomyces boulardii*, yet more preferably said at least one yeast is selected from the group comprising or consisting of *Saccharomyces bayanus* var. *uvarum, Saccharomyces bayanus* var. *bayanus, Saccharomyces cerevisiae, Saccharomyces boulardii* and yet more preferably said at least one yeast is selected from the group comprising or consisting of *Saccharomyces bayanus* var. *uvarum* MUCL 55125 (deposited in BCCM/MUCL Louvain-La-Neuve); *Saccharomyces bayanus* MUCL 31491 (obtained from BCCM/MUCL Louvain-La-Neuve), *Saccharomyces bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group), *Saccharomyces cerevisiae* w-34/70 (obtained from Fermentis, Lesaffre group), and *Saccharomyces boulardii* (obtained from Enterol®; biocodex gamma), and yet more preferably *Saccharomyces bayanus* var. *uvarum* MUCL 55125 (deposited in BCCM/MUCL Louvain-La-Neuve).

55. A composition comprising fructan, sucrose and at least one yeast selected from the group consisting of *Saccharomyces bayanus, Saccharomyces cerevisiae*, and *Kluyveromyces lactis*.

56. A composition comprising fructan, sucrose and at least one yeast selected from the group consisting of *Saccharomyces bayanus, Saccharomyces cerevisiae*, and *Kluyveromyces lactis*, wherein said composition comprises sucrose and at least 30 wt % of fructan based on the total dry matter weight of said composition.

57. A yeast deposited in the Belgian Co-ordinated Collections of Micro-Organisms (BCCM) with accession number MUCL 55125.

58. Use of a yeast according to statement 57 for reducing the amount of free sugars including sucrose in a composition comprising fructan and sucrose, more preferably for reducing the amount of sucrose in a composition comprising sucrose and at least 30 wt % of fructan based on the total dry matter weight of said composition.

59. Use of a yeast selected from the group consisting of *Saccharomyces* and *Kluyveromyces* for reducing the amount of free sugars including sucrose in a composition comprising fructan and sucrose, more preferably for reducing the amount of sucrose in a composition comprising sucrose and at least 30 wt % of fructan based on the total dry matter weight of said composition.

60. A method for reducing the amount of free sugars including sucrose in a composition comprising fructan and sucrose comprising the step of using the method according to any one of statements 1 to 54.

61. A method for purifying a composition comprising fructan and sucrose comprising the step of using the method according to any one of statements 1 to 54.

62. A method for storing a composition comprising fructan and sucrose comprising the step of using the method according to any one of statements 1 to 54.

63. A method for treating a composition comprising fructan and sucrose comprising the step of using the method according to any one of statements 1 to 54.

64. A method for removing free sugars, from a composition comprising fructan and sucrose comprising the step of using the method according to any one of statements 1 to 54.

65. A method for reducing the amount free sugars, from a composition comprising fructan and sucrose comprising the step of using the method according to any one of statements 1 to 54.

66. A method for eliminating free sugars, from a composition comprising fructan and sucrose comprising the step of using the method according to any one of statements 1 to 54.

67. A method for fermenting free sugars, from a composition comprising fructan and sucrose comprising the step of using the method according to any one of statements 1 to 54.

68. Use of a yeast selected from the group consisting of *Saccharomyces*, and *Kluyveromyces* for reducing the amount of free sugars including sucrose in a composition comprising fructan and sucrose, more preferably for reducing the amount of sucrose in a composition comprising sucrose and at least 30 wt % of fructan based on the total dry matter weight of said composition or any one or more of the statements 1 to 54.

69. Use according to any one of statements 59 or 68, wherein said yeast is selected from the group comprising or consisting of *Saccharomyces bayanus, Saccharomyces cerevisiae, Kluyveromyces lactis*, and *Saccharomyces boulardii*; yet more preferably said at least one yeast is selected from the group comprising or consisting of *Saccharomyces bayanus* var. *uvarum, Saccharomyces bayanus* var. *bayanus, Saccharomyces cerevisiae, Saccharomyces boulardii*, and *Kluyveromyces lactis* var. *drosophylarum*, yet more preferably said at least one yeast is selected from the group comprising or consisting of *Saccharomyces bayanus* var. *uvarum* MUCL 55125 (deposited in BCCM/MUCL Louvain-La-Neuve); *Saccharomyces bayanus* MUCL 31491 (obtained from BCCM/ MUCL Louvain-La-Neuve), *Saccharomyces bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group), *Kluyveromyces lactis* var. *drosophylarum* CBS 2103 (obtained from CBS-KNAW fungal biodiversity center, Utrecht NL), *Saccharomyces cerevisiae* w-34/70 (obtained from Fermentis, Lesaffre group), and *Saccharomyces boulardii* (obtained from Enterol®; biocodex gamma).

70. Method or use according to any one of the previous statements, wherein said yeast is *Saccharomyces bayanus*, preferably *Saccharomyces bayanus* var. *uvarum* MUCL 55125 (deposited in BCCM/MUCL Louvain-La-Neuve); *Saccharomyces bayanus* MUCL 31491 (obtained from BCCM/MUCL Louvain-La-Neuve), *Saccharomyces bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group), 71. Method or use according to any one of the previous statements, wherein said composition comprising fructan and sucrose is incubated with *Kluyveromyces*; preferably *Kluyveromyces lactis*, more preferably *Kluyveromyces lactis* var. *drosophylarum*, for example *Kluyveromyces lactis* var. *drosophylarum* CBS 2103 (e.g. obtained from CBS-KNAW fungal biodiversity center, Utrecht NL), at a temperature below 35° C., preferably below 32° C., more preferably below 24° C., such as from −5° C. to 35° C., for example from 2° C. to 35° C., for example from −5° C. to 32° C., for example from 2° C. to 32° C., for example from −5° C. to 24° C., for example from 2° C. to 24° C.

72. Method or use according to any one of the previous statements, wherein said composition comprising fructan and sucrose is incubated with *Kluyveromyces*; preferably *Kluyveromyces lactis*, more preferably *Kluyveromyces lactis* var. *drosophylarum*, for example *Kluyveromyces lactis* var. *drosophylarum* CBS 2103 (e.g. obtained from CBS-KNAW fungal biodiversity center, Utrecht NL) at a pH above 4.7, preferably above 5.7, such as from 4.7 to 8, for example from 5.7 to 8, for example from 4.7 to 7, or for example from 5.7 to 7.

73. Method or use according to any one of statements 1 to 72, wherein said yeast is *Saccharomyces bayanus*.

74. Method or use according to statement 73, wherein said yeast is selected from the group comprising or consisting of *Saccharomyces bayanus* var. *uvarum* MUCL 55125; *Saccharomyces bayanus* MUCL 31491, *Saccharomyces bayanus* MUCL 31495, *Saccharomyces bayanus* BC S103, and *Saccharomyces bayanus* VR 44.

In a first aspect, the present invention relates to a method for processing a composition comprising fructan and sucrose, preferably inulin and sucrose, comprising the step of incubating a composition comprising fructan and sucrose, wherein said composition comprising fructan and sucrose comprises at least 30 wt % of fructan based on the total dry matter weight of said composition, with at least one yeast selected from the group comprising or consisting of *Saccharomyces* and *Kluyveromyces*, until a reduction of at least 10% of the initial weight of sucrose in said composition is obtained; as well as the combined or separate use of these one or more yeasts for the above stated purpose. Said reduction of at least 10% of the initial weight of sucrose in said composition can be measured by liquid chromatography such as for example using High Performance Anion Exchange Chromatography coupled with Pulse Amperometric Detection (HPAEC-PAD).

In another aspect, the present invention relates to a method for purifying a composition comprising fructan and sucrose, preferably inulin and sucrose, comprising the step of incubating a composition comprising fructan and sucrose, wherein said composition comprising fructan and sucrose comprises at least 30 wt % of fructan based on the total dry matter weight of said composition, with at least one yeast selected from the group comprising or consisting of *Saccharomyces* and *Kluyveromyces* until a reduction of at least 10% of the initial weight of sucrose in said composition is obtained; as well as the combined or separate use of these one or more yeasts for the above stated purpose.

In another aspect, the present invention relates to a method for treating a composition comprising fructan and sucrose, preferably inulin and sucrose, comprising the step of incubating a composition comprising fructan and sucrose, wherein said composition comprising fructan and sucrose comprises at least 30 wt % of fructan based on the total dry matter weight of said composition, with at least one yeast selected from the group comprising or consisting of *Saccharomyces* and *Kluyveromyces* until a reduction of at least 10% of the initial weight of sucrose in said composition is obtained; as well as the combined or separate use of these one or more yeasts for the above stated purpose.

In another aspect, the present invention relates to a method for storing a composition comprising fructan and sucrose, preferably inulin and sucrose, comprising the step of incubating a composition comprising fructan and sucrose, wherein said composition comprising fructan and sucrose comprises at least 30 wt % of fructan based on the total dry matter weight of said composition, with at least one yeast selected from the group comprising or consisting of *Saccharomyces* and *Kluyveromyces* until a reduction of at least 10% of the initial weight of sucrose in said composition is obtained; as well as the combined or separate use of these one or more yeasts for the above stated purpose, and storing said composition.

In a further aspect, the present invention relates to a method for removing sugars, preferably free sugars including sucrose, more preferably carbohydrate monomers and/or carbohydrate dimers, most preferably hexose and/or pentose monomers or dimers, most preferably sucrose, glucose and/or fructose, from a composition comprising fructan and sucrose preferably inulin and sucrose, comprising the step of incubating a composition comprising fructan and sucrose, wherein said composition comprising fructan and sucrose comprises at least 30 wt % of fructan based on the total dry matter weight of said composition, with at least one yeast selected from the group comprising or consisting of *Saccharomyces* and *Kluyveromyces* until a reduction of at least 10% of the initial weight of sucrose in said composition is obtained; as well as the combined or separate use of these one or more yeasts for the above stated purpose.

In a further aspect, the present invention relates to a method for reducing the amount of sugars, preferably free sugars, more preferably carbohydrate monomers and/or carbohydrate dimers, most preferably hexose and/or pentose monomers or dimers, most preferably sucrose, glucose and/or fructose, from a composition comprising fructan and sucrose preferably inulin and sucrose, comprising the step of incubating a composition comprising fructan and sucrose, wherein said composition comprising fructan and sucrose comprises at least 30 wt % of fructan based on the total dry matter weight of said composition, with at least one yeast selected from the group comprising or consisting of *Saccharomyces* and *Kluyveromyces* until a reduction of at least 10% of the initial weight of sucrose in said composition is obtained; as well as the combined or separate use of these one or more yeasts for the above stated purpose.

In a further aspect, the present invention relates to a method for eliminating sugars, preferably free sugars, more preferably carbohydrate monomers and/or carbohydrate dimers, most preferably hexose and/or pentose monomers or dimers, most preferably sucrose, glucose and/or fructose, from a composition comprising fructan and sucrose, preferably inulin and sucrose, comprising the step of incubating a composition comprising fructan and sucrose, wherein said composition comprising fructan and sucrose comprises at least 30 wt % of fructan based on the total dry matter weight of said composition, with at least one yeast selected from the group comprising or consisting of *Saccharomyces* and *Kluyveromyces* until a reduction of at least 10% of the initial weight of sucrose in said composition is obtained; as well as the combined or separate use of these one or more yeasts for the above stated purpose.

In a further aspect, the present invention relates to a method for fermenting sugars, preferably free sugars, more preferably carbohydrate monomers and/or carbohydrate dimers, most preferably hexose and/or pentose monomers or dimers, most preferably sucrose, glucose and/or fructose, from a composition comprising fructan and sucrose, preferably inulin and sucrose, comprising the step of incubating a composition comprising fructan and sucrose, wherein said composition comprising fructan and sucrose comprises at least 30 wt % of fructan based on the total dry matter weight of said composition, with at least one yeast selected from the group comprising or consisting of *Saccharomyces* and *Kluyveromyces* until a reduction of at least 10% of the initial weight of sucrose in said composition is obtained; as well as the combined or separate use of these one or more yeasts for the above stated purpose.

As used herein, the term "incubating" or "incubated" refers to contacting the yeast as described herein with the composition comprising fructan and sucrose, preferably inulin and sucrose, as described herein and preferably maintaining such mixture under specific conditions in order to promote a particular reaction, in particular fermentation. It is to be understood that if live yeasts are used, incubation parameters are set such that viability of the yeast, at least during a specified time, is assured.

As used herein, the term "fructan" relates to polymers of fructose molecules. A glucose unit at what would otherwise be the reducing-end may be present in fructans. The linkage position of the fructose residues can determine the type of the fructan. Linkage can occur at one of the two primary hydroxyls (OH-1 or OH-6). Fructan for use in the present invention encompasses the two basic types of simple fructan: inulins (in which the fructosyl residues are generally linked by β-2,1-linkages) and levans (in which the fructosyl residues are generally linked by β-2,6-linkages). Also encompassed herein are graminian or mixed fructans which have both β-2,1 and β-2,6 linkage bonds between the fructose units, and thus contain branches. In plants up to 1000 fructose units can be linked in a single fructan-molecule. Fructan for use in the present invention can also encompass microbial fructans which can comprise up to 100.000 fructose units. Fructan for use in the present invention can be found in plants, algae and bacteria. Fructans are a type of dietary fiber. Fructans for use in the present invention can be industrially mainly obtained from chicory roots (*Cichorium intybus*) or from the Jerusalem artichoke (*Helianthus tuberosus*). Degradation products of inulin are fructooligosaccharides (FOS), i.e. hydrolysis of inulins may yield fructooligosaccharides, which are oligomers with a DP generally below 20, which are also encompassed herein. Fructooligosaccharides can also be enzymatically synthesized from sucrose.

As used herein, the term "inulin" refers to a mixture of oligo- and/or polysaccharides of fructose which may have a terminal glucose. Inulins belong to a class of fibers known as fructans. In an embodiment, inulin can be represented, depending from the terminal carbohydrate unit, by the general formulae $GF_n$ and/or $F_m$, wherein G represents a glucose unit, F represents a fructose unit, n is an integer representing the number of fructose units linked to the terminal glucose unit, and m is an integer representing the number of fructose units linked to each other in the carbohydrate chain, preferably wherein n is at least 2, and m is at least 2. Inulins for use in the present invention encompass inulins with a terminal glucose which are also referred as alpha-D-glucopyranosyl-[beta-D-fructofuranosyl](n−1)-D-fructofuranosides, as well as inulins without glucose which are also referred as beta-D-fructopyranosyl-[D-fructofuranosyl](n−1)-D-fructofuranosides. Inulins for use in the present invention can also encompass branched inulin. Inulins for use in the present invention can also encompass the hydrolysis products of inulins such as fructo-oligosaccharides (FOS), also called oligofructoses, which are fructose oligomers with a DP of ≤20, and they can also encompass fructo-oligosaccharides ending with a terminal glucose with a DP of 3-5 synthesized from sucrose. Preferably said fructo-oligosaccharides have an average DP by number of at least 3 and at most 7. Suitable saccharide chains of inulin from plant origin for use in the invention can have a DP ranging from 2 to about 100. Inulin can be a liquid or a powder product.

As used herein, the terms "degree of polymerization" or "(DP)" relates to the number of monosaccharide residues present in an oligo- or polysaccharide. Often also the parameter average degree of polymerization is used. The degree of polymerization is a measure of molecular weight (MW). The DP can be calculated as the ratio of the total MW of the polymer or oligomer and the MW of the repeating units.

The average degree of polymerization (av DP) of a (polydispersed) oligo- or polysaccharide mixture is the mean of the degree of polymerization (DP) of all the molecules present in this saccharide mixture. The average degree of polymerization herein, unless otherwise specified, is calculated based on the number of molecules for each DP: av DPn or average degree of polymerization by number as described herein below.

Determination of the molecular mass distribution of the fructan sample is done by High Performance Anion Exchange Chromatography coupled with Pulse Amperometric Detection (HPAEC-PAD) on a Thermo scientific—Dionex ICS 5000 chromatographic system. Separation of the various chain lengths is achieved by a Carbopac PA100 4 mm*250 mm (+guard) at 40° C. with a flow rate of 1 ml/min. Sodium hydroxide 160 mM is used as eluent. A gradient of sodium acetate during the run allows to separate the various chain lengths.

Fructan mixture standards at different concentrations are injected in order to draw the calibration curves and to assign the peaks in the chromatogram based on the retention time of the standard. The calibration curves allow determining the concentration of each molecular species in the sample.

From the obtained concentration distribution, the average polymerization degree in number $\overline{Dp_n}$ is calculated as $$\overline{Dp_n} = \frac{\sum_i N_i Dp_i}{\sum_i N_i}$$

Where Ni is the number of molecules having i residue and Dpi the number of residue.

In an embodiment, the fructan as described herein, preferably inulin, has an average DP by number of at least 3. In an embodiment, the fructan as described herein, preferably inulin, has an average DP by number of at most 500. In an embodiment, said fructan, preferably inulin, has an average DP by number of at least 3, for example of at least 5, for example of at least 7, for example of at least 10, for example at least 15, for example at least 20, for example at least 25, for example at least 70. In an embodiment, the fructan as described herein, preferably inulin, has an average DP by number of at least 3 and of at most 500, preferably of at least 3 and at most 100, more preferably of at least 3 and of at most 30. In a further preferred embodiment, the fructan as described herein, preferably inulin, comprises or consists of fructooligosaccharides (FOS). In a further preferred embodiment, the fructan as described herein has an average DP by number of at least 3 and at most 20, preferably of at least 3 and at most 15, such as of at least 3 and at most 10. In yet another preferred embodiment, the fructan as described herein, preferably inulin, comprises or consists of hydrolyzed or partially hydrolyzed fructan, preferably inulin. Hydrolyzed fructan, such as hydrolyzed inulin, may for instance be obtained enzymatically (e.g. by inulinases) or may alternatively be obtained by acid and/or thermal hydrolysis.

In an embodiment, the fructan, preferably inulin, as described herein is derived from or isolated from plants, i.e. it is of plant origin, preferably from Chicory (*Cichorium intybus*), Agave (*Agave* spp.), Banana (*Musa* spp.), Burdock (*Arctium lappa*), Camas (*Camassia* spp.), Coneflower (*Echinacea* spp.), *Saussurea Costus lappa*, Dandelion (*Taraxacum ruderalia*), Elecampane (*Inula helenium*), Garlic (*Allium sativum*), Jerusalem artichoke (*Helianthus tuberosus*), Jicama (*Pachyrhizus erosus*), Leopard's-bane (*Arnica montana*), Mugwort (*Artemisia vulgaris*), Onion (*Allium cepa*), Wild yam (*Dioscorea* spp.), Yacón (*Smallanthus sonchifolius* spp.), Leak (*Allium porum*), Asparagus, Scorzonera hispanica, Salsify (*Tragopogon porrifolius*), Wheat (*Tritichum aestivum*), Dahlia (*Dahlia* spp.), most preferably from Chicory.

In an embodiment, the composition comprising fructan and sucrose is obtained by hot water extraction. In a preferred embodiment, industrial production of fructan, such as inulin from for instance chicory root involves extraction by hot water. However, free sugars (such as glucose, fructose and sucrose) are co-extracted.

As used herein, the term "free sugars" refers to monosaccharides and/or disaccharides. Free sugars may for instance be present in plants, plant material, or plant homogenates, extracts, or isolates, or fractionated plant material. In a preferred embodiment, the term "free sugars" as used herein refers to hexose or pentose mono- or di-saccharides, preferably hexose mono- or di-saccharides. Most preferably, the term "free sugars" encompasses fructose, glucose, and sucrose (saccharose). Accordingly, in an embodiment, free sugars comprise or consist or consist essentially of fructose. In another embodiment, free sugars comprise or consist or consist essentially of glucose. In yet another embodiment, free sugars comprise or consist or consist essentially of sucrose. In a further embodiment, free sugars comprise or consist of fructose and glucose. In yet another embodiment, free sugars comprise or consist or consist essentially of fructose and sucrose. In another embodiment, free sugars comprise or consist or consist essentially of glucose and sucrose. In yet a further embodiment, free sugars comprise or consist or consist essentially of fructose, glucose, and sucrose.

In embodiments, in the methods as described herein, the composition comprising fructan and sucrose, preferably inulin and sucrose, further comprises one or more free sugars, as defined above.

As used herein, the term "composition comprising fructan and sucrose" or "composition comprising inulin and sucrose" refers to any type of composition which contains fructan or inulin respectively and sucrose. Such composition may be a dry composition. Preferably, such composition is a liquid composition, most preferably an aqueous composition (i.e. a composition comprising water and a certain amount of fructan, preferably inulin, dissolved and/or dispersed therein). The compositions may be obtained by homogenizing for instance plant material. Preferably, the compositions as described herein refer to extracts, which are enriched in fructan, preferably inulin, compared to the source material it is derived from. Inulin extraction may for instance involve putting plant material in hot water followed by concentration (e.g. evaporation). In an embodiment, the compositions comprising fructan and sucrose, preferably inulin and sucrose, as described herein comprise at least 30 wt % of fructan, preferably inulin, based on the total dry matter weight of the composition, preferably at least 40 wt %, preferably at least 50 wt %, preferably at least 60 wt % of fructan, for example at least 30 g of fructan, preferably inulin, per 100 g of dry matter. In an embodiment, the compositions comprising fructan and sucrose, preferably inulin and sucrose, as described herein comprise at least 1.5 wt % of fructan based on the total weight of the composition, preferably inulin; preferably at least 5.0 wt % of fructan, preferably inulin; more preferably at least 8.0 wt % of fructan, preferably inulin. In another embodiment, the compositions comprising fructan and sucrose, preferably inulin and sucrose, as described herein comprise at most 80 wt % of fructan; preferably inulin, based on the total weight of the composition. In an embodiment, the compositions comprising fructan and sucrose, preferably inulin and sucrose, as described herein comprise at most 70 wt %, for example at most 60 wt %, for example at most 50 wt % of fructan, preferably inulin; for example at most 45 wt % of fructan, preferably inulin based on the total weight of the composition. In a preferred embodiment, the compositions comprising fructan and sucrose, preferably inulin and sucrose, as described herein comprise at least 1.5 wt % of fructan and at most 80 wt % of fructan, preferably inulin, i.e. at least 1.5 g and at most 80 g of fructan, preferably inulin per 100 g of composition. In an embodiment, the compositions comprising fructan and sucrose, preferably inulin and sucrose, as described herein comprise at least 5 wt % and at most 70 wt % of fructan based on the total weight of the composition; preferably inulin, preferably at least 8 wt % and at most 65 wt % of fructan, preferably inulin; more preferably at least 8 wt % and at most 50 wt % of fructan, preferably inulin; even more preferably at least 8 wt % and at most 45 wt % of fructan, preferably inulin.

The composition comprising fructan and sucrose, such as inulin rich extract, can be obtained by hot water extraction of a plant material. The plant material for example chicory roots is first harvested and then can be washed and if necessary sliced into cossettes (strips or slices). Hot water extraction can be performed by counter current diffusion with hot water of the plant material, preferably of the sliced plant material. Typical plant material (e.g. cossettes) to water ratio can be for example 1. Suitable temperature can be of at least 50° C., for example at least 60° C., for example at least 70° C. Typical extraction time may vary from 1 to 10 hours. The resulting juice containing fructan in solution may if needed be roughly filtered in order to remove exhausted plant material.

Preferably, the composition of step (a) is obtained using a method comprising the steps of (i) hot water extraction of a fructan comprising material, (ii) filtration of the hot water extract; and (iii) demineralization of the filtrate of step (ii) thereby recovering a composition comprising fructan and sucrose of step (a). In some embodiment, the composition of step (a) is obtained using a method comprising the steps of (i) hot water extraction of a fructan comprising material, (ii) filtration of the hot water extract; (iii) demineralization of the filtrate of step (ii); and (iv) active carbon filtration of the filtrate of step (iii) thereby recovering a composition comprising fructan and sucrose of step (a).

One example of resulting composition comprising fructan and sucrose, preferably inulin and sucrose, can have a typical dry matter content of 13% and comprise about 77 wt % of inulin based on dry matter basis, and about 9 wt % of free sugars (including sucrose).

The yeasts which may be used in the methods as described herein are selected from the group comprising or consisting of *Saccharomyces* and *Kluyveromyces*; preferably, the yeasts are selected from the group comprising or consisting of *Saccharomyces bayanus; Saccharomyces cerevisiae; Kluyveromyces lactis*, and *Saccharomyces boulardii* or selected from the group comprising or consisting of *Saccharomyces bayanus; Kluyveromyces lactis*, and *Saccharomyces boulardii*, or selected from the group comprising or consisting of *Saccharomyces bayanus* and *Saccharomyces boulardii*; yet more preferably the yeasts are selected from the group comprising or consisting of *Saccharomyces bayanus* var. *uvarum*, (for example *S. bayanus* MUCL 55125 (deposited at BCCM/MUCL Louvain-La-Neuve) or MUCL 31491 (obtained from BCCM/MUCL Louvain-La-Neuve), *Saccharomyces bayanus* var. *bayanus* (for example, *S. bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group), *Saccharomyces cerevisiae* (for example *S. cerevisiae* w-34/70 (obtained from Fermentis, Lesaffre group), *Saccharomyces boulardii* (obtained from Enterol®, biocodex gamma), and *Kluyveromyces lactis* var. *drosophylarum*, (for example *Kluyveromyces lactis* var. *drosophylarum* CBS 2103 (obtained from CBS-KNAW fungal biodiversity center, Utrecht NL). In a preferred embodiment, the yeast is *Saccharomyces bayanus*, preferably *Saccharomyces bayanus* var. *uvarum* or *Saccharomyces bayanus* var. *bayanus*, preferably *Saccharomyces bayanus* var. *uvarum* MUCL 55125 (deposited in BCCM/MUCL Louvain-La-Neuve); *Saccharomyces bayanus* var. *bayanus* MUCL 31495 (obtained from BCCM/MUCL Louvain-La-Neuve), or *Saccharomyces bayanus* var. *uvarum* MUCL 31491 (obtained from BCCM/MUCL Louvain-La-Neuve), most preferably *Saccharomyces bayanus* var. *uvarum* MUCL 55125 (deposited in BCCM/MUCL Louvain-La-Neuve). In particular, *Saccharomyces bayanus* appears to be very versatile in connection with the incubation conditions, in that it performs very well under a wide range of conditions.

In some embodiments, in the methods as described herein, the composition comprising fructan and sucrose, preferably inulin, and sucrose, further comprises one or more additional free sugars (including sucrose), as defined above in an amount of at least 1 wt %, preferably at least 3 wt %, based on the total weight of the dry matter of the composition, and for example at most 70 wt % of free sugars (including the sucrose). More preferably at least 1 wt % and at most 60 wt % free sugars (including sucrose), based on dry matter, more preferably at least 3 wt % and at most 50 wt %, based on dry matter. As used herein, the term "based on dry matter" refers to the wt % of a respective component on the dry matter content of the composition (e.g. 1 wt % based on dry matter refers to 1 g per 100 g dry matter).

Total dry matter can be determined gravimetrically as residue remaining after drying. Typically moisture is evaporated from sample by oven drying. Typically 5 g of sample is weighed in a dry aluminium dish previously weighed (precision balance Ohaus, capacity 410 g, sensitivity 0.001 g). The sample is placed in an oven at 103° C. until the residual weight remains constant (at least 24 h). Sample is cooled in a desiccator for 1 h and then immediately weighted. Results are expressed in % (g of dry matter per 100 g of sample).

Dry matter (%)=$(m3-m1)/(m2-m1)\times100$ $m1$=weight of the dry aluminium dish (in g)
$m2$=weight of the aluminium dish with the sample before drying (in g)
$m3$=weight of the aluminium dish with the sample after drying (in g)

Preferably, the compositions comprising fructan and sucrose comprise at least 1.5 wt % fructan, preferably inulin, based on the total weight of the composition. Preferably, these compositions comprise at most 80 wt % fructan, preferably inulin, based on the total weight of the composition. Preferably, these compositions comprise at least 1.5 wt % and at most 75 wt % fructan, preferably inulin, as indicated above.

Further preferred embodiments illustrating the amounts of free sugars based on dry weight of the composition, at the start of the incubation step, in particular fructose, glucose and sucrose which may be present in the compositions comprising fructan and sucrose as described herein are depicted in Table 1 below.

TABLE 1

| Embodiment | sucrose | fructose | glucose |
|---|---|---|---|
| 1. | ≥1 wt % | | |
| 2. | ≥1.5 wt % | | |
| 3. | 1-10 wt % | | |
| 4. | 1.5-8 wt % | | |
| 5. | ≥1 wt % | ≥1 wt % | |
| 6. | ≥1.5 wt % | 1-10 wt % | |
| 7. | 1-10 wt % | ≥1 wt % | |
| 8. | 1-10 wt % | 1-10 wt % | |
| 9. | 1.5-8 wt % | 1-10 wt % | |
| 10. | ≥1 wt % | ≥1 wt % | ≥0.5 wt % |
| 11. | ≥1.5 wt % | ≥1 wt % | ≥0.5 wt % |
| 12. | 1-10 wt % | 1-10 wt % | 0.5-3 wt % |
| 13. | 1.5-8 wt % | 1-10 wt % | 0.5-3 wt % |
| 14. | ≥1 wt % | ≥1 wt % | 0.5-3 wt % |
| 15. | 1-10 wt % | 1-10 wt % | ≥0.5 wt % |
| 16. | ≥1 wt % | ≥1 wt % | |
| 17. | 1-10 wt % | 1-10 wt % | |

TABLE 1-continued

| Embodiment | sucrose | fructose | glucose |
|---|---|---|---|
| 18. | ≥1 wt % | ≥1 wt % | |
| 19. | 1-10 wt % | 1-10 wt % | |
| 20. | ≥1.5 wt % | | ≥0.5 wt % |
| 21. | 1.5-8 wt % | | 0.5-3 wt % |
| 22. | 1.5-8 wt % | | ≥0.5 wt % |
| 23. | ≥1.5 wt % | | 0.5-3 wt % |
| 24. | ≥1.5 wt % | ≥1 wt % | ≥0.5 wt % |
| 25. | 1.5-8 wt % | 1-10 wt % | 0.5-3 wt % |
| 26. | ≥1.5 wt % | ≥1 wt % | 0.5-3 wt % |
| 27. | 1.5-8 wt % | 1-10 wt % | ≥0.5 wt % |
| 28. | 1.5-8 wt % | ≥1 wt % | 0.5-3 wt % |
| 29. | ≥1.5 wt % | 1-10 wt % | ≥0.5 wt % |
| 30. | 1.5-8 wt % | ≥1 wt % | ≥0.5 wt % |
| 31. | ≥1.5 wt % | 1-10 wt % | 0.5-3 wt % |

In an embodiment, in the compositions comprising fructan and sucrose, preferably inulin and sucrose, as described herein, the weight ratio based on dry weight of sucrose and other free sugars, at the start of the incubation, preferably the weight ratio based on dry weight of sucrose and one or more of fructose, and glucose, preferably all, to fructan, preferably inulin, is at least 1:100 and at most 2.3:1, more preferably at least 1:50 and at most 2:1. In further embodiments, in the compositions comprising fructan and sucrose, preferably inulin, and sucrose as described herein, the weight ratio of free sugars, preferably the embodiments as described in Table 1, to fructan, preferably inulin, is at least 1:10 and at most 1.5:1, more preferably at least 1:5 and at most 1:1.

In some optional embodiments, prior and/or during step (b) a nitrogen source can be added to said composition comprising fructan and sucrose, preferably inulin and sucrose. The nitrogen source may be an organic (e.g. peptone) and/or inorganic (e.g. nitrate) nitrogen source. In an embodiment, the nitrogen source may be provided as a composition comprising further additives, such as additional nutrients, minerals, etc. In a preferred embodiment, the nitrogen source is yeast extract. In an embodiment, the amount of nitrogen source is at least 0.01 wt %, expressed as ammonium equivalent, and for example at most 1 wt % (based on the total weight of the composition), preferably at least 0.03 wt % and at most 1.0 wt %, more preferably at least 0.05 wt % and at most 1.0 wt %.

In some optional embodiments, each of the methods as described herein may further comprise the step of aerating the composition comprising fructan and sucrose, preferably inulin and sucrose, preferably after addition of the yeast as defined herein, at the start of the incubation, and/or during incubation with the yeast as defined herein. It is to be understood that the term "aeration" in the present context relates to process by which an oxygen containing gas, preferably air, is circulated through, mixed with or dissolved in the composition comprising fructan and sucrose, preferably inulin and sucrose, as defined herein. By means of further guidance, and without limitation, aeration can be accomplished by passing air through the liquid by means of a Venturi tube, aeration turbines or compressed air which can be combined with diffuser(s) air stone(s), as well as fine bubble diffusers, coarse bubble diffusers or linear aeration tubing. Preferred aeration rates are at least 0.01 vvm and at most 1 vvm (gas volume flow per unit of liquid volume per minute), preferably at least 0.05 vvm and at most 1.0 vvm. In an embodiment, when the yeast is *Saccharomyces*, such as *Saccharomyces bayanus*, no aeration is provided. In another embodiment, when the yeast is *Kluyveromyces* such as *Kluyveromyces lactis*, aeration is provided.

In embodiments, each of the methods as described herein may further comprise the step of agitating the composition comprising fructan and sucrose, preferably inulin and sucrose, preferably after addition of the yeast as defined herein and/or during incubation with the yeast as defined herein. It is to be understood that the term "agitating" in the present context relates to process by which the composition as defined herein is put in motion, and hence is mixed. By means of further guidance, agitation may be effected by shaking, stirring, rotating, or pumping the liquid around. For instance a magnetic agitator or a stirring rod may be used to effect agitation.

In further embodiments, each of the methods as described herein may further comprise the step of aerating and agitating the composition comprising fructan and sucrose, preferably inulin and sucrose, preferably after addition of the yeast as defined herein and/or during incubation with the yeast as defined herein, wherein aeration and agitation are as defined above. It is to be understood that aeration may encompass agitation and vice versa. For instance introduction of air into the composition may set the composition into motion and hence effect agitation. The other way around, for instance agitation by means of an impeller may introduce simultaneously air into the composition.

In further embodiments, each of the methods as described herein may further comprise the step of removing the yeast after the incubation step, preferably after a specified time as defined herein elsewhere, such as for instance also indicated in Table 2. Removal of yeast from the compositions after incubation as defined herein is well known in the art. Without limitation, removal of the yeast may be effected by for instance centrifugation, decantation, and/or filtration.

In some embodiments, in each of the methods as described herein the composition comprising fructan and sucrose, preferably inulin and sucrose, is incubated with the at least one yeast as defined herein at a temperature above the freezing point of said composition, preferably at a temperature which is optimal for the respective yeast, preferably at a temperature 10° C. higher or lower than the temperature which is optimal for the respective yeast. Optimal temperatures for the yeasts as defined herein are known in the art. By means of further guidance, and without limitation, an optimal temperature as defined herein refers to the temperature at which growth is maximized. In a preferred embodiment, in each of the methods as described herein, the yeast as defined herein is incubated with the composition comprising fructan and sucrose, preferably inulin and sucrose, at a temperature of at least −5° C. In a preferred embodiment, in each of the methods as described herein, the yeast as defined herein is incubated with the composition comprising fructan and sucrose, preferably inulin and sucrose, at a temperature of at most 40° C. In a preferred embodiment, in each of the methods as described herein, the yeast as defined herein is incubated with the composition comprising fructan and sucrose, preferably inulin and sucrose, at a temperature of at least −5° C. and at most 40° C., more preferably at a temperature of at least 2° C. and at most 35° C. In a further preferred embodiment, the incubation is performed at a temperature of at least 15° C. and at most 35° C., such as at least 20° C. and at most 30° C., for instance 30° C. or about 30° C. In yet another preferred embodiment, the incubation is performed at a temperature of at least −5° C. and at most 15° C., such as at least 4° C. and at most 10° C.

In embodiments, in each of the methods as described herein the composition comprising fructan and sucrose, preferably inulin and sucrose, is incubated with the at least one yeast as defined herein at a temperature less than 35° C., preferably less than 32° C. more preferably less than 24° C. In embodiments, in each of the methods as described herein the composition comprising fructan and sucrose, preferably inulin and sucrose, is incubated with the at least one yeast as defined herein at a temperature less than 35° C., preferably less than 32° C., more preferably less than 24° C., and more than −5° C., preferably more than 2° C. In embodiments, in each of the methods as described herein the composition comprising fructan and sucrose, preferably inulin and sucrose, is incubated with *Kluyveromyces*; preferably *Kluyveromyces lactis*, more preferably *Kluyveromyces lactis* var. *drosophylarum*, for example *Kluyveromyces lactis* var. *drosophylarum* CBS 2103 (e.g. obtained from CBS-KNAW fungal biodiversity center, Utrecht NL), at a temperature less than 35° C., preferably less than 32° C., more preferably less than 24° C. In embodiments, in each of the methods as described herein the composition comprising fructan and sucrose, preferably inulin and sucrose, is incubated with the at least one yeast as defined herein at a temperature less than 35° C., preferably less than 32° C., more preferably less than 24° C., and more than −5° C., preferably more than 2° C. In embodiments, in each of the methods as described herein the composition comprising fructan and sucrose, preferably inulin and sucrose, is incubated with *Kluyveromyces*; preferably *Kluyveromyces lactis*, more preferably *Kluyveromyces lactis* var. *drosophylarum*, (for example *Kluyveromyces lactis* var. *drosophylarum* CBS 2103 (e.g. obtained from CBS-KNAW fungal biodiversity center, Utrecht NL) at a temperature less than 35° C., preferably less than 32° C., more preferably less than 24° C., and more than −5° C., preferably more than 2° C.

In embodiments, in each of the methods as described herein the composition comprising fructan and sucrose, preferably inulin and sucrose, is incubated with at least one yeast as defined herein for at least 5 hours, such as for at least 10 hours, at least 15 hours; at least 50 hours, for instance at least 75 hours; at least 4 days (i.e. 4×24 hours), such as at least 10 days; at least 30 days, for instance at least 60 days, or at least 90 days, or at least 120 days. In embodiments, in each of the methods as described herein the composition comprising fructan and sucrose, preferably inulin and sucrose, is incubated with the yeast as defined herein for at most 12 months, for example for at most 6 months, for example at most 4 months, such as at most 180 days, for example at most 150 days, such as at most 30 days (i.e. 30×24 hours), such as at most 20 days; at most 150 hours, at most 125 hours; at most 50 hours, for instance at most 30 hours, or at most 25 hours.

In embodiments, in each of the methods as described herein the composition comprising fructan and sucrose, preferably inulin and sucrose, is incubated with the yeast as defined herein for at least 5 hours and at most 12 months, preferably for at least 5 hours and at most 6 months, such as at least 5 hours and at most 4 months, for instance at least 10 hours and at most 30 hours or at least 15 hours and at most 25 hours; at least 50 hours and at most 150 hours, for instance at least 75 hours and at most 125 hours; at least 4 days (i.e. 4×24 hours) and at most 30 days (i.e. 30×24 hours), such as at least 10 and at most 20 days; at least 30 days and at most 180 days, for instance at least 60 days and 150 days, or at least 90 days and at most 180 days, or at least 120 and at most 150 days.

Preferred combinations of temperature and time of incubation of the compositions comprising fructan and sucrose, preferably inulin and sucrose, with the at least one yeast as described herein are illustrated as embodiments in Table 2.

TABLE 2

| Embodiment | Temperature (° C.) | Time |
|---|---|---|
| 1a | −5 to 10 | ≥8 days for example 8 days-12 months |
| 2a | 4 to 12 | ≥5 days for example 5 days-12 months |
| 3a | 6 to 16 | ≥3 days for example 3 days-6 months |
| 4a | 8 to 20 | ≥1 day for example 1 day-60 days |
| 5a | 15 to 20 | ≥1 day for example 1-15 days |
| 6a | 17 to 25 | ≥5 hours for example 5 hours-10 days |
| 7a | 20 to 30 | ≥5 hours for example 5 hours-7 days |
| 8a | 25 to 35 | ≥5 hours for example 5 hours-5 days |
| 9a | 30 to 35 | ≥5 hours for example 5 hours-5 days |
| 10a | −5 to 35 | ≥5 hours for example 5 hours-12 months |
| 11a | −5 to 32 | ≥5 hours for example 5 hours-12 months |
| 12a | 2 to 35 | ≥5 hours for example 5 hours-12 months |
| 13a | 2 to 32 | ≥5 hours for example 5 hours-12 months |
| 14a | −5 to 24 | ≥5 hours for example 5 hours-12 months |
| 15a | 2 to 24 | ≥5 hours for example 5 hours-12 months |
| 16a | 17 to 24 | ≥5 hours for example 5 hours-10 days |

The skilled person will understand that the above embodiments may be combined. For example, the composition may be incubated at a temperature of at least 4° C. and at most 25° C., for example for at least 5 hours to at most 12 months, whereby, in some embodiments, if the incubation temperature is between 4° C. and 12° C., the composition may be incubated for at least 5 days, such as for at least 5 days and at most 12 months; in some embodiments, if the incubation temperature is at least 6° C. to at most 16° C., the composition may be incubated for at least 3 days, such as for at least 3 days and at most 6 months; in some embodiments, if the incubation temperature is at least 8° C. to at most 20° C., the composition may be incubated for at least 1 day, such as for at least 1 day and at most 60 days; in some embodiments if the incubation temperature is of at least 15° C. to at most 20° C., the composition may be incubated for at least 1 day, such as at least 1 day and at most 15 days; and in some embodiments, if the temperature is at least 17° C. to at most 25° C., the composition may be incubated for at least 5 hours, such as for at least 5 hours and at most 10 days.

In the embodiments 1a-16a above, the yeasts may be selected from the group comprising or consisting of *Saccharomyces* and *Kluyveromyces*; preferably, the yeasts are selected from the group comprising or consisting of *Saccharomyces bayanus*; *Saccharomyces cerevisiae*; *Kluyveromyces lactis*, and *Saccharomyces boulardii*, or selected from the group comprising or consisting of *Saccharomyces bayanus*; *Kluyveromyces lactis*, and *Saccharomyces boulardii*, or selected from the group comprising or consisting of *Saccharomyces bayanus* and *Saccharomyces boulardii*; yet more preferably the yeasts are selected from the group comprising or consisting of *Saccharomyces bayanus* var. *uvarum*, (for example *S. bayanus* MUCL 55125 (deposited at BCCM/MUCL Louvain-La-Neuve) or MUCL 31491 (obtained from BCCM/MUCL Louvain-La-Neuve), *Saccharomyces bayanus* var. *bayanus* (for example, *S. bayanus*

MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group), *Saccharomyces cerevisiae* (for example *S. cerevisiae* w-34/70 (obtained from Fermentis, Lesaffre group), *Saccharomyces boulardii* (obtained from Enterol®, biocodex gamma), and *Kluyveromyces lactis* var. *drosophylarum*, (for example *Kluyveromyces lactis* var. *drosophylarum* CBS 2103 (obtained from CBS-KNAW fungal biodiversity center, Utrecht NL). In a preferred embodiment, the yeast is *Saccharomyces bayanus*, preferably *Saccharomyces bayanus* var. *uvarum* or *Saccharomyces bayanus* var. *bayanus*, preferably *Saccharomyces bayanus* var. *uvarum* MUCL 55125 (deposited in BCCM/MUCL Louvain-La-Neuve); *Saccharomyces bayanus* var. *bayanus* MUCL 31495 (obtained from BCCM/MUCL Louvain-La-Neuve), or *Saccharomyces bayanus* var. *uvarum* MUCL 31491 (obtained from BCCM/MUCL Louvain-La-Neuve), most preferably *Saccharomyces bayanus* var. *uvarum* MUCL 55125 (deposited in BCCM/MUCL Louvain-La-Neuve). In particular, *Saccharomyces bayanus* appears to be very versatile in connection with the incubation conditions, in that it performs very well under a wide range of conditions. Embodiments 10a-13a above are particularly suited for use with *Kluyveromyces*, preferably *Kluyveromyces lactis*, more preferably *Kluyveromyces lactis* var. *drosophylarum*, for example *Kluyveromyces lactis* var. *drosophylarum* CBS 2103, e.g. obtained from CBS-KNAW fungal biodiversity center, Utrecht NL.

In further embodiments, in each of the methods as described herein the composition comprising fructan and sucrose, preferably inulin and sucrose, is incubated with the yeast as defined herein for a time sufficient to reduce one or more of the initial total weight of free sugars (including sucrose) concentration (based on dry weight) by at least 10%. This reduction can be achieved by using one or more incubation steps. Preferably, said composition comprising fructan and sucrose is incubated with said at least one yeast until a reduction of at least 20% of the initial weight of free sugars (including sucrose) in said composition is achieved, for example at least 30%, for example at least 40%, for example at least 50%; for example by at least 60%, for example by at least 70%, for example by at least 80%, preferably at least 90%, preferably at least 95%, for example at least 98%, for example a reduction of at least 99%. In further embodiments, in each of the methods as described herein the composition comprising fructan and sucrose, preferably inulin and sucrose, is incubated with the yeast as defined herein for a time sufficient to reduce the fructose concentration (based on dry weight) by at least 10%, for example at least 20%, for example at least 30%, for example at least 40%, for example at least 50%; for example by at least 60%, for example by at least 70%, for example by at least 80%, preferably at least 90%, preferably at least 95%, for example at least 98%, for example a reduction of at least 99%. In further embodiments, in each of the methods as described herein the composition comprising fructan and sucrose, preferably inulin and sucrose, is incubated with the yeast as defined herein for a time sufficient to reduce the glucose concentration (based on dry weight) by at least 10%, for example at least 20%, for example at least 30%, for example at least 40%, for example at least 50%; for example by at least 60%, for example by at least 70%, for example by at least 80%, preferably at least 90%, preferably at least 95%, for example at least 98%, for example a reduction of at least 99%. In further embodiments, in each of the methods as described herein the composition comprising fructan and sucrose, preferably inulin and sucrose, is incubated with the yeast as defined herein for a time sufficient to reduce the sucrose concentration (based on dry weight) by at least 10%, for example at least 20%, for example at least 30%, for example at least 40%, for example at least 50%; for example by at least 60%, for example by at least 70%, for example by at least 80%, preferably at least 90%, preferably at least 95%, for example at least 98%, for example a reduction of at least 99%. In further embodiments, in each of the methods as described herein the composition comprising fructan and sucrose, preferably inulin and sucrose, is incubated with the yeast as defined herein for a time sufficient to reduce the combined fructose and glucose concentration (based on dry weight) by at least 10%, for example at least 20%, for example at least 30%, for example at least 40%, for example at least 50%; for example by at least 60%, for example by at least 70%, for example by at least 80%, preferably at least 90%, preferably at least 95%, for example at least 98%, for example a reduction of at least 99% wt %. In further embodiments, in each of the methods as described herein the composition comprising fructan and sucrose, preferably inulin and sucrose, is incubated with the yeast as defined herein for a time sufficient to reduce the combined fructose and sucrose concentration (based on dry weight) by at least 10%, for example at least 20%, for example at least 30%, for example at least 40%, for example at least 50%; for example by at least 60%, for example by at least 70%, for example by at least 80%, preferably at least 90%, preferably at least 95%, for example at least 98%, for example a reduction of at least 99%. In further embodiments, in each of the methods as described herein the composition comprising fructan and sucrose, preferably inulin and sucrose, is incubated with the yeast as defined herein for a time sufficient to reduce the combined glucose and sucrose concentration (based on dry weight) by at least 10%, for example at least 20%, for example at least 30%, for example at least 40%, for example at least 50%; for example by at least 60%, for example by at least 70%, for example by at least 80%, preferably at least 90%, preferably at least 95%, for example at least 98%, for example a reduction of at least 99%. In further embodiments, in each of the methods as described herein the composition comprising fructan and sucrose, preferably inulin and sucrose, is incubated with the yeast as defined herein for a time sufficient to reduce the combined fructose, glucose and sucrose concentration (based on dry weight) by at least 10%, for example at least 20%, for example at least 30%, for example at least 40%, for example at least 50%; for example by at least 60%, for example by at least 70%, for example by at least 80%, preferably at least 90%, preferably at least 95%, for example at least 98%, for example a reduction of at least 99%. The times necessary for reaching the set free sugar (including sucrose) concentrations can be determined empirically, as known in the art.

In embodiments, in each of the methods as described herein the composition comprising fructan and sucrose, preferably inulin and sucrose, is incubated with the yeast as defined herein at a pH at least 2.5, preferably at least 3.0. In embodiments, in each of the methods as described herein the composition comprising fructan and sucrose, preferably inulin and sucrose, the yeast as defined herein is incubated with the composition comprising fructan and sucrose, preferably inulin and sucrose; at a pH of at least 2.5, for example at least 3.0, for example at least 3.5, for example at least 4.0 for example at least 5.0. In embodiments, in each of the methods as described herein the composition comprising fructan and sucrose, preferably inulin and sucrose, is incubated with the yeast as defined herein at a pH of at most 8.5, preferably at most 7.5. In embodiments, in each of the methods as described herein the composition comprising fructan and sucrose, preferably inulin and sucrose, the yeast as defined herein is incubated with the composition comprising fructan and sucrose, preferably inulin and sucrose, at a pH of at most 8.0, for example at most 7.5, for example at most 7.0, for example at most 6.5 for example at most 6.0. In embodiments, in each of the methods as described herein the composition comprising fructan and sucrose, preferably inulin and sucrose, is incubated with the yeast as defined herein at a pH of at least 2.5 and at most 8.0, preferably at least 3.0 and at most 7.5. In embodiments, in each of the methods as described herein the composition comprising fructan and sucrose, preferably inulin and sucrose, the yeast as defined herein is incubated with the composition comprising fructan and sucrose, preferably inulin and sucrose, at a pH of at least 4 and at most 7.0, for example at least 4.5 and at most 6.0, for example at least 5 and at most 7.0, for example at least 5.5 and at most 7.0. The pH can be set and maintained as is known in the art.

In embodiments, in each of the methods as described herein the composition comprising fructan and sucrose, preferably inulin and sucrose, is incubated with the yeast as defined herein at a pH of at least 4.7, preferably a pH of at least 5.7. In some embodiments, in each of the methods as described herein the composition comprising fructan and sucrose, preferably inulin and sucrose, is incubated with the yeast as defined herein at a pH of at least 4.7, preferably a pH of at least 5.7, and a pH of at most 8.0, preferably pH of at most 7.0. In embodiments, in each of the methods as described herein the composition comprising fructan and sucrose, preferably inulin and sucrose, is incubated with *Kluyveromyces*; preferably *Kluyveromyces lactis*, more preferably *Kluyveromyces lactis* var. *drosophylarum*, for example *Kluyveromyces lactis* var. *drosophylarum* CBS 2103 (e.g. obtained from CBS-KNAW fungal biodiversity center, Utrecht NL), preferably at a pH of at least 4.7, preferably a pH of at least 5.7. In embodiments, in each of the methods as described herein the composition comprising fructan and sucrose, preferably inulin and sucrose, is incubated with *Kluyveromyces*; preferably *Kluyveromyces lactis*, more preferably *Kluyveromyces lactis* var. *drosophylarum*, (for example *Kluyveromyces lactis* var. *drosophylarum* CBS 2103, e.g. obtained from CBS-KNAW fungal biodiversity center, Utrecht NL, preferably at a pH of at least 4.7, preferably at a pH of at least 5.7, and a pH of at most 8.0, preferably a pH of at most 7.0.

In some embodiments, in each of the methods as described herein the composition comprising fructan and sucrose, preferably inulin and sucrose, is incubated with the yeast as defined herein at a pH of at least 4.7, preferably a pH of at least 5.7, and a temperature below 35° C., preferably below 32° C., more preferably below 24° C. In embodiments, in each of the methods as described herein the composition comprising fructan and sucrose, preferably inulin and sucrose, is incubated with the yeast as defined herein at a pH of at least 4.7, preferably a pH of at least 5.7, and a pH of at most 8.0, preferably a pH of at most 7.0, and a temperature of at most 35° C., preferably at most 32° C., more preferably at most 24° C., and a temperature of at least −5° C., preferably at least 2° C. In some embodiments, in each of the methods as described herein the composition comprising fructan and sucrose, preferably inulin and sucrose, is incubated with *Kluyveromyces*; preferably *Kluyveromyces lactis*, more preferably *Kluyveromyces lactis* var. *drosophylarum*, for example *Kluyveromyces lactis* var. *drosophylarum* CBS 2103, e.g. obtained from CBS-KNAW fungal biodiversity center, Utrecht NL, at a pH of at least 4.7, preferably a pH of at least 5.7, and a temperature of at most 35° C., preferably at most 32° C., more preferably at most 24° C. In embodiments, in each of the methods as described herein the composition comprising fructan and sucrose, preferably inulin and sucrose, is incubated with *Kluyveromyces*; preferably *Kluyveromyces lactis*, more preferably *Kluyveromyces lactis* var. *drosophylarum*, for example *Kluyveromyces lactis* var. *drosophylarum* CBS 2103, e.g. obtained from CBS-KNAW fungal biodiversity center, Utrecht NL, at a pH of at least 4.7, preferably a pH of at least 5.7, and a pH of at most 8.0, preferably a pH of at most 7.0, and a temperature of at most 35° C., preferably at most 32° C., more preferably at most 24° C. and a temperature of at least −5° C., preferably at least 2° C.

In some embodiments, in each of the methods as described herein the composition comprising fructan and sucrose, preferably inulin and sucrose, is incubated with the yeast as defined herein at a pH of at least 2.5. In embodiments, in each of the methods as described herein the composition comprising fructan and sucrose, preferably inulin and sucrose, is incubated with the yeast as defined herein at a pH of at least 2.5, and a pH of at most 7.0, preferably a pH of at most 5.0. In some embodiments, in each of the methods as described herein the composition comprising fructan and sucrose, preferably inulin and sucrose, is incubated with *Saccharomyces*; preferably *Saccharomyces bayanus*, more preferably *Saccharomyces bayanus* var. *uvarum*, (for example *S. bayanus* MUCL 55125 (deposited at BCCM/MUCL Louvain-La-Neuve) or MUCL 31491 (obtained from BCCM/MUCL Louvain-La-Neuve), *Saccharomyces bayanus* var. *bayanus* (for example, *S. bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group) at a pH of at least 2.5. In embodiments, in each of the methods as described herein the composition comprising fructan and sucrose, preferably inulin and sucrose, is incubated with *Saccharomyces*; preferably *Saccharomyces bayanus*, more preferably *Saccharomyces bayanus* var. *uvarum*, (for example *S. bayanus* MUCL 55125 (deposited at BCCM/MUCL Louvain-La-Neuve) or MUCL 31491 (obtained from BCCM/MUCL Louvain-La-Neuve), *Saccharomyces bayanus* var. *bayanus* (for example, *S. bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group) at a pH of at least 2.5, and a pH of at most 7.0, preferably a pH of at most 5.0.

In embodiments, in each of the methods as described herein the composition comprising fructan and sucrose, preferably inulin and sucrose, is incubated with the yeast as defined herein at a pH of at least 2.5, and a temperature of at most 35° C., preferably of at most 32° C., more preferably of at most 24° C. In embodiments, in each of the methods as described herein the composition comprising fructan and sucrose, preferably inulin and sucrose, is incubated with the yeast as defined herein at a pH of at least 2.5, and a pH of at most 7.0, preferably a pH of at most 5.0, and a temperature of at most 35° C., preferably of at most 32° C., more preferably of at most 24° C., and a temperature of at least −5° C., preferably of at least 2° C. In embodiments, in each of the methods as described herein the composition comprising fructan and sucrose, preferably inulin and sucrose, is incubated with *Saccharomyces*; preferably *Saccharomyces bayanus*, more preferably *Saccharomyces bayanus* var.

*uvarum*, (for example *S. bayanus* MUCL 55125 (deposited at BCCM/MUCL Louvain-La-Neuve) or MUCL 31491 (obtained from BCCM/MUCL Louvain-La-Neuve), *Saccharomyces bayanus* var. *bayanus* (for example, *S. bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group) at a pH of at least 2.5, and a temperature of at most 35° C., preferably of at most 32° C., more preferably of at most 24° C. In embodiments, in each of the methods as described herein the composition comprising fructan and sucrose, preferably inulin and sucrose, is incubated with *Saccharomyces*; preferably *Saccharomyces bayanus*, more preferably *Saccharomyces bayanus* var. *uvarum*, (for example *S. bayanus* MUCL 55125 (deposited at BCCM/MUCL Louvain-La-Neuve) or MUCL 31491 (obtained from BCCM/MUCL Louvain-La-Neuve), *Saccharomyces bayanus* var. *bayanus* (for example, *S. bayanus* MUCL 31495 (obtained from BCCM/MUCL Louvain-La-Neuve), *Saccharomyces bayanus* BC S103 (obtained from Fermentis, Lesaffre group), *Saccharomyces bayanus* VR 44 (obtained from Fermentis, Lesaffre group) at a pH of at least 2.5, and a pH of at most 7.0, preferably pH of at most 5.0, and a temperature of at most 35° C., preferably of at most 32° C., more preferably at most 24° C. and a temperature of at least −5° C., preferably at least 2° C.

In embodiments, in each of the methods as described herein the composition comprising fructan and sucrose, preferably inulin and sucrose, is incubated with the yeast as defined herein, wherein at least $10^3$ CFU of yeast is added at the start of the incubation per ml of composition comprising fructan and sucrose, preferably inulin and sucrose. In embodiments, in each of the methods as described herein the composition comprising fructan and sucrose, preferably inulin and sucrose, is incubated with the yeast as defined herein, wherein at most $10^{10}$ CFU of yeast is added at the start of the incubation per ml of composition comprising fructan and sucrose, preferably inulin and sucrose. In embodiments, in each of the methods as described herein the composition comprising fructan and sucrose, preferably inulin and sucrose, is incubated with the yeast as defined herein, wherein at least $10^3$ CFU and at most $10^{10}$ colony forming units CFU of yeast is added at the start of the incubation per ml of composition comprising fructan and sucrose, preferably inulin and sucrose. Colony forming units are well known in the art and can for instance be determined by plate counting. For instance may be added to the compositions as defined herein at least $10^3$ CFU/ml and at most $10^9$ CFU/ml, for example at least $10^4$ CFU/ml and at most $10^9$ CFU/ml, for example at least $10^5$ CFU/ml and at most $10^9$ CFU/ml, for example at least $10^4$ CFU/ml and at most $10^8$ CFU/ml, for example at least $10^4$ CFU/ml and at most $10^9$ CFU/ml, for example at least $10^5$ CFU/ml and at most $10^8$ C/ml. Advantageously, the above concentrations of yeast may be combined with the specific time and temperature embodiments as described in Table 2, or the specific times or temperatures as described earlier.

In embodiments, in each of the methods as described herein the composition comprising fructan and sucrose, preferably inulin and sucrose, is incubated with the yeast as defined herein, wherein the yeast is provided as a yeast lysates or an extract of the yeast, such as a protein or enzyme extract. It is to be understood that for determining the amount of such lysates or extract, the corresponding quantities as the amount of CFU/ml as described above are to be incubated with the compositions.

In a most preferred embodiment, in each of the methods as described herein, the composition is a liquid composition comprising fructan and sucrose, preferably inulin and sucrose, which is incubated with *Saccharomyces*, preferably *Saccharomyces bayanus*, preferably *Saccharomyces bayanus* var. *uvarum*, wherein the composition comprises at least 1 wt % and at most 70 wt % (based on dry matter) of sucrose and other free sugars (including sucrose), preferably at least 1 wt % and at most 70 wt % (based on dry matter) of sucrose and one or more of fructose, and glucose, preferably a mixture of all, based on the total weight of the dry matter of the composition.

In a further most preferred embodiment, in each of the methods as described herein the composition is a liquid composition comprising fructan and sucrose, preferably inulin and sucrose, most preferably comprising at least 30 wt % of fructan, preferably inulin, based on the total dry matter weight of the composition, and preferably comprising at least 1 wt % and at most 75 wt % (based on dry matter) of sucrose and optionally other free sugars (including sucrose), more preferably comprises at least 1 wt % and at most 75 wt % (based on dry matter) of sucrose and one or more of fructose and glucose, preferably a mixture of all. Preferably, the composition is incubated with *Saccharomyces bayanus*, preferably *Saccharomyces bayanus* var. *uvarum*, at a temperature of at least −5° C. and at most 40° C., preferably at a temperature of at least 0.0° C. and at most 35° C.

In a further most preferred embodiment, in each of the methods as described herein the composition is a liquid composition comprising fructan and sucrose, preferably inulin and sucrose, most preferably at least 30 wt % and at most 99 wt % of fructan, preferably inulin, based on the total dry matter weight of the composition, said composition being incubated with *Saccharomyces bayanus*, preferably *Saccharomyces bayanus* var. *uvarum*, wherein the composition comprises at least 1 wt % and at most 75 wt % (based on dry matter) of sucrose and optionally other free sugars, preferably sucrose and one or more of fructose and glucose, preferably a mixture of all, wherein said composition is incubated at a temperature of at least −5° C. and at most 40° C., preferably at a temperature of at least 0.0° C. and at most 35° C.

In an aspect, the invention also relates to a composition comprising fructan and sucrose, preferably inulin and sucrose and at least one yeast selected from the group comprising or consisting of *Saccharomyces bayanus* (preferably *Saccharomyces bayanus* var. *uvarum*), *Kluyveromyces lactis* (preferably *Kluyveromyces lactis* var. *drosophylarum*, most preferably *Kluyveromyces lactis* var. *drosophylarum* CBS 2103 (obtained from CBS-KNAW fungal biodiversity center, Utrecht NL). In a preferred embodiment, the yeast is *Saccharomyces bayanus*, preferably *Saccharomyces bayanus* var. *uvarum*. The embodiments described earlier in connection with the fructan compositions (in particular relating to the type, quantity, origin, composition, DP, as well as the embodiments relating to the free sugars, their types, and quantities) equally apply to the compositions of this aspect.

In a further aspect, the invention relates to a yeast deposited in the Belgian Co-ordinated Collections of Micro-Organisms (BCCM) with accession number MUCL 55125. It is to be understood that this yeast is most preferred in the compositions, methods and uses according to the invention as described herein elsewhere.

The present invention also encompasses a composition comprising fructan, sucrose and at least one yeast selected from the group consisting of *Saccharomyces bayanus, Sac-* charomyces cerevisiae, and *Kluyveromyces lactis*, wherein said composition comprises at least 30 wt % of fructan based on the total dry matter weight of said composition.

In yet another aspect, the invention relates to the use of a yeast for removing, reducing, or eliminating sugars, preferably free sugars, more preferably carbohydrate monomers and/or carbohydrate dimers, most preferably hexose and/or pentose monomers or dimers from a composition comprising fructan and sucrose, preferably inulin and sucrose, wherein said yeast is selected from the group comprising or consisting of *Saccharomyces* and *Kluyveromyces*; preferably selected from the group comprising or consisting of *Saccharomyces bayanus; Saccharomyces cerevisiae; Kluyveromyces lactis; Saccharomyces boulardii*, or selected from the group comprising or consisting of *Saccharomyces bayanus; Kluyveromyces lactis*, and *Saccharomyces boulardii*, or selected from the group comprising or consisting of *Saccharomyces bayanus* and *Saccharomyces boulardii*; yet more preferably *Saccharomyces bayanus* var. *uvarum*, (for example *Saccharomyces bayanus* MUCL 55125 (deposited in BCCM/MUCL Louvain-La-Neuve) or MUCL 31491 (obtained in BCCM/MUCL Louvain-La-Neuve), *Saccharomyces bayanus* var. *bayanus* (for example, *S. bayanus* MUCL 31495 (obtained in BCCM/MUCL Louvain-La-Neuve), *Saccharomyces cerevisiae* (for example *S. cerevisiae* w-34/70 (obtained from Fermentis, Lesaffre group), *Saccharomyces boulardii* (obtained from Enterol®, biocodex gama) and *Kluyveromyces lactis* var. *drosophylarum*, (most preferably *Kluyveromyces lactis* var. *drosophylarum* CBS 2103 (obtained from CBS-KNAW fungal biodiversity center, Utrecht NL); yet more preferably *Saccharomyces bayanus* var. *uvarum*, (for example *Saccharomyces bayanus* MUCL 55125 (deposited in BCCM/MUCL Louvain-La-Neuve) or MUCL 31491 (obtained in BCCM/MUCL Louvain-La-Neuve), *Saccharomyces bayanus* var. *bayanus* (for example, *S. bayanus* MUCL 31495 (obtained in BCCM/MUCL Louvain-La-Neuve), *Saccharomyces cerevisiae* (for example *S. cerevisiae* w-34/70 (obtained from Fermentis, Lesaffre group), *Saccharomyces boulardii* (obtained from Enterol®, biocodex gama); yet more preferably *Saccharomyces bayanus* var. *uvarum* MUCL 55125 (deposited in BCCM/MUCL Louvain-La-Neuve). Preferably, the free sugars are selected from one or more of fructose, glucose, and sucrose, preferably all. The embodiments described earlier in connection with the fructan compositions (in particular relating to the type, quantity, origin, composition, (average) DP, as well as the embodiments relating to the free sugars, their types, and quantities), as well as the time and temperature of incubation equally apply to the compositions of this aspect.

The present invention also encompasses the use of a yeast selected from the group consisting of *Saccharomyces* and *Kluyveromyces* for reducing the amount of sucrose in a composition comprising sucrose and at least 30 wt % of fructan based on the total dry matter weight of said composition.

The aspects and embodiments of the invention are further supported by the following non-limiting examples.

EXAMPLES

Protocols
Dry Matter Measurement

Total dry matter was determined gravimetrically as residue remaining after drying. Moisture was evaporated from sample by oven drying.

5 g of sample were weighed in a dry aluminium dish previously weighed (precision balance Ohaus, capacity 410 g, sensitivity 0.001 g). The sample was placed in an oven at 103° C. until the residual weight remained constant (at least 24 h). Sample was cooled in a desiccator for 1 h and then immediately weighed. Results were expressed in % (g of dry matter per 100 g of sample).

$$\text{Dry matter } (\%) = (m3 - m1)/(m2 - m1) \times 100$$

m1=weight of the dry aluminium dish (in g)
m2=weight of the aluminium dish with the sample before drying (in g)
m3=weight of the aluminium dish with the sample after drying (in g)

Determination of the Molecular Mass Distribution of the Inulin

Determination of the molecular mass distribution of the inulin sample was done by High Performance Anion Exchange Chromatography coupled with Pulse Amperometric Detection (HPAEC-PAD) on a Thermo scientific—Dionex ICS 5000 chromatographic system. Separation of the various chain lengths was achieved by a Carbopac PA100 4 mm*250 mm (+guard) at 40° C. with a flow rate of 1 ml/min. Sodium hydroxide 160 mM was used as eluent. A gradient of sodium acetate during the run allowed separating the various chain lengths. The software allowed determining each corresponding peak area in nC*min.

Average Dp in Number Determination

Different concentrations of a standard inulin were injected in order to assign the peaks in the chromatogram based on the retention time of the standard and to draw the calibration curves.

The calibration curves allowed determining the mass concentration of each molecular inulin species in the sample Ci. The molar concentration (Ni) of the molecules having i residues was calculated as Ci/MWi, where MWi is the molecular weight the molecules having i residues The average polymerization degree in number $\overline{Dp_n}$ was calculated as $$\overline{Dp_n} = \frac{\sum_i N_i Dp_i}{\sum_i N_i}$$

Where Dpi is the number of residues.
Free Sugars Determination

In a weighed bottle (Schott), about 5 g of a representative sample (m4 to 0.001 g) were accurately weighed. Then about 10 g of phosphate buffer (0.1M) at pH=7.0 were added and the sample was heated at 80° C. for 15 minutes in a water bath. Next, the sample was cooled down to room temperature and the total weight of the solution was brought to 40 g with demineralized water (m5 to 0.001 g).

The first dilution factor was D1=m5/m4.

Finally, appropriate dilutions (D2) for HPAEC-PAD analyses with suitable calibration (glucose, fructose, sucrose) were made.

The amounts of free glucose, free fructose and free sucrose were determined by multiplying the results from HPAEC-PAD by D1*D2 and are expressed in g/kg of the sample or in wt % based on the dry matter.

Inulin Amount Determination
Principle

The inulin amount was determined from the amount of glucose and fructose released by enzymatic hydrolysis. Free glucose, fructose and sucrose were first determined on a non-hydrolyzed representative sample. Then enzymatic hydrolysis was performed and the total glucose and fructose were determined. The released amounts were obtained by difference taking into account the glucose and fructose amounts released from sucrose.

The method was based on the AOAC997.08 method with slight adaptations as described below.

Determination of the Free Sugars

The amounts of free glucose (Gf), free fructose (Ff) and free sucrose (S) were determined by HPAEC-PAD as described here above.

Enzymatic Hydrolysis—Total Fructose and Total Glucose Determination

In a weighted beaker, about 1 g of a representative sample (m6 to 0.001 g) was accurately weighed. Then about 20 g of acetate buffer (0.1M) at pH 4.75 was added and the mixture was homogenized. After, the sample was heated at 80° C. for 15 minutes in a water bath and was cooled down to 60° C. in a water bath (allowed to equilibrate). Next, 50 μL of Fructozyme (Novozym SP 230®, Novo Nordisk) were added and the mixture was homogenized. Then the bottle was closed and the mixture was incubated in a water bath at 60° C. for 2 hours. The sample was cooled down to room temperature and the mass of the solution was brought to 40 g with demineralized water (m7 to 0.001 g). Finally the sample was homogenized.

The first dilution factor is D3=m7/m6

Appropriate dilutions (D4) for HPAEC-PAD analyses with suitable calibration (glucose and fructose) were made.

The amounts of total glucose (Gt) and total fructose (Ft) were determined by multiplying the results from HPAEC-PAD by D3*D4 and were expressed in g/kg of the initial composition.

Calculations

The glucose released from the inulin fraction is Gi=Gt−Gf−S/1.9 (in g/kg)

The fructose released from the inulin fraction is Fi=Ft−Ff−S/1.9 (in g/kg)

The inulin amount in the sample is k(Gi+Fi)

Where k is a factor taking into account the dry matter increase due to the hydrolysis of inulin. In our examples k was set to 0.91.

Inulin Loss

The inulin loss was defined as the difference between the amount of inulin before and after yeast incubation expressed in mass percentage of the initial amount.

Determination of Organic Acids

Determination of the acid organic concentration was done by High Performance Liquid Chromatography system (LCM1 Waters) comprising UV detector (Waters 2487), autosampler (Waters 717) and controller (Waters 600). Separation of peaks was achieved by a HPX-87H Biorad column at 65° C. with a flow rate of 0.8 ml/min. $H_2SO_4$ 0.0045 N was used as eluent.

The calibration line was obtained by injection of 10 μl, 25 μl, 40 μl, 50 μl of a stock solution of 1 g/l of different acids to be assayed. The calibration curves allowed determining the concentration of each molecular species in the sample. 25 μl of the sample was injected for an analysis time of 20 minutes.

Determination of Alcohols and Volatiles Components

Determination of the alcohols and volatiles components was done by Gas Chromatography coupled with FID detector on a Perkin-Elmer 8000 chromatographic system. Separation of peaks was achieved by a CP WAX-52 column. The analysis was done using the technique of Head Space. The gas phase in equilibrium with the liquid phase was injected into the Gas Chromatography according to a temperature program (pre-heating: 60° C./20 min; heating: rise of 60° per minute up to 110°; injector (HS40 Perkin-Elmer) temperature: 110° C.; FID detector temperature: 250° C.).

Mixture of volatiles components standards at different concentrations were injected in order to draw the calibration curves and to assign the peaks in the chromatogram based on the retention time of the standard. The calibration curves allowed to determine the concentration of each molecular species in the sample.

Preparation of Compositions Comprising Fructan and Sucrose (Inulin Rich Extract)—Step (a).

Compositions A1-A3

Chicory roots were washed and sliced into cossettes. Counter current diffusion with hot water (70° C.) was then used to extract the inulin from the cossettes. Cossettes to water ratio was 1. Extraction time was 2 hours. The resulting juice containing inulin in solution was roughly filtered in order to remove exhausted cossettes. The resulting juice was further filtered to remove small insoluble material. The pH was adjusted to 4 with HCl 25%. A concentration step at 100° C. during 1 hour allowed increasing the dry matter to 40 wt/wt %, thereby preparing compositions A1-A3.

Composition F

Chicory roots were washed and sliced into cossettes. Counter current diffusion with hot water (70° C.) was then used to extract the inulin from the cossettes. Cossettes to water ratio was 1. Extraction time was 2 hours. The resulting juice containing inulin in solution was roughly filtered in order to remove exhausted cossettes. The resulting juice was further filtered to remove small insoluble material. A concentration step at 100° C. during 1 hour allowed increasing the dry matter to 40 wt/wt %, thereby preparing composition F.

Preparation of Compositions Comprising Fructan and Sucrose (Inulin Rich Compositions)—Step (a)

Compositions B1-B7

217 g of Fibruline® instant (commercially available from Cosucra group Warcoing) were suspended in 1 kg phosphate buffer solution pH 5.8.

The phosphate buffer was prepared as follows: 467.5 ml of $KH_2PO_4$ 0.2 mol/l solution and 32.5 ml of $K_2HPO_4$ 0.2 mol/l were mixed together. Then the mixture was made up to 1 L with distilled water.

90 g of the Fibruline® Instant suspension were put in a 250 ml flask and sterilized (20 min, 121° C.), thereby preparing compositions B1-B7.

Composition C 434 g of Fribuline® instant (commercially available from Cosucra group Warcoing) were suspended in 2 kg of demineralized water. Then 1800 g of the Fibruline® instant suspension were added in the 2 L bioreactor and sterilized (20 min, 121° C.), thereby preparing composition C.

Composition D 31.5 kg of Fribulose® F90 (commercially available from Cosucra group Warcoing) were suspended in 40 kg of demineralized water. Then 40 kg of the Fibrulose® F90 suspension were added in a 60 L barrel, thereby preparing composition D. The composition D was not sterilized.

Composition E 10.5 kg of Fibrulose® F90 (commercially available from Cosucra group Warcoing) were suspended in 40 kg of demineralized water. Then 40 kg of the Fibrulose® F90 suspension were added in the 60 L barrel, thereby preparing composition E. The composition E was not sterilized.

The concentration of inulin and free sugars of compositions A-F are listed in Table 3.

TABLE 3

| Composition | Dry matter wt/wt % based on the total weight of the composition | Inulin wt/wt % based on the total dry matter | Glucose wt/wt % based on total dry matter | Fructose wt/wt % based on total dry matter | Sucrose wt/wt % based on total dry matter |
|---|---|---|---|---|---|
| A1 | 40 | 64.1 | 1.4 | 13.2 | 7.3 |
| A2 | 40 | 62.3 | 1.6 | 14.2 | 7.9 |
| A3 | 40 | 62.1 | 1.7 | 13.9 | 8.3 |
| B1 | 17 | 88.8 | 1.0 | 4.3 | 5.9 |
| B2 | 17 | 89.1 | 1.1 | 4.1 | 5.7 |
| B3 | 17 | 88.7 | 1.0 | 4.4 | 5.9 |
| B4 | 17 | 88.4 | 1.0 | 4.5 | 6.1 |
| B5 | 17 | 89.4 | 0.9 | 3.8 | 5.9 |
| B6 | 17 | 89.3 | 1.0 | 3.9 | 5.8 |
| B7 | 17 | 88.3 | 1.0 | 3.6 | 7.1 |
| C | 17 | 89.7 | 0.8 | 3.3 | 6.2 |
| D | 42 | 89.9 | 0.7 | 3.0 | 6.4 |
| E | 20 | 88.1 | 1.1 | 4.2 | 6.6 |
| F | 40 | 78.9 | 0.3 | 1.3 | 5.5 |

Example 1

Specificity of Different Yeasts for a Composition Comprising Inulin, Sucrose and Other Free Sugars—Step (b)

A yeast extract solution was prepared as follows: 10 g of yeast extract (Merck) were dissolved in 100 ml of demineralized water. Then the solution was sterilized (20 min, 121° C.).

10 g of the sterilized yeast extract solution were added to 90 g of composition B1-B5 respectively. No supplemental aeration was provided.

Compositions B1-B5, complemented with yeast extract, were inoculated at a concentration of $10^5$ CFU/ml with different yeasts, respectively: Saccharomyces cerevisiae w-34/70 (from Fermentis, Lesaffre group), Kluyveromyces lactis CBS 2103 (from CBS-KNAW fungal biodiversity center, Utrecht NL), Saccharomyces bayanus var. bayanus MUCL 31495 (from MUCL Louvain-La-Neuve, Belgium), Saccharomyces bayanus var. uvarum MUCL 31491 (from MUCL Louvain-La-Neuve, Belgium) and Saccharomyces bayanus var. uvarum MUCL 55125 (deposited in the Belgian Co-ordinated Collections of Micro-Organisms (BCCM) under accession number MUCL 55125). The compositions were incubated at different temperatures (20° C. and 30° C.) under a stirring rate of 160 rpm. The results of these experiments are shown in FIGS. 1 to 15.

FIGS. 1, 2, 3 and 4 show the growth (measured as optical density at 660 nm) over time at 30° C. of Saccharomyces cerevisiae w-34/70, Kluyveromyces lactis CBS 2103, Saccharomyces bayanus var. bayanus MUCL 31495, and Saccharomyces bayanus var. uvarum MUCL 31491, respectively, incubated with compositions B1-B4 respectively in 250 ml flask.

Figure 5:
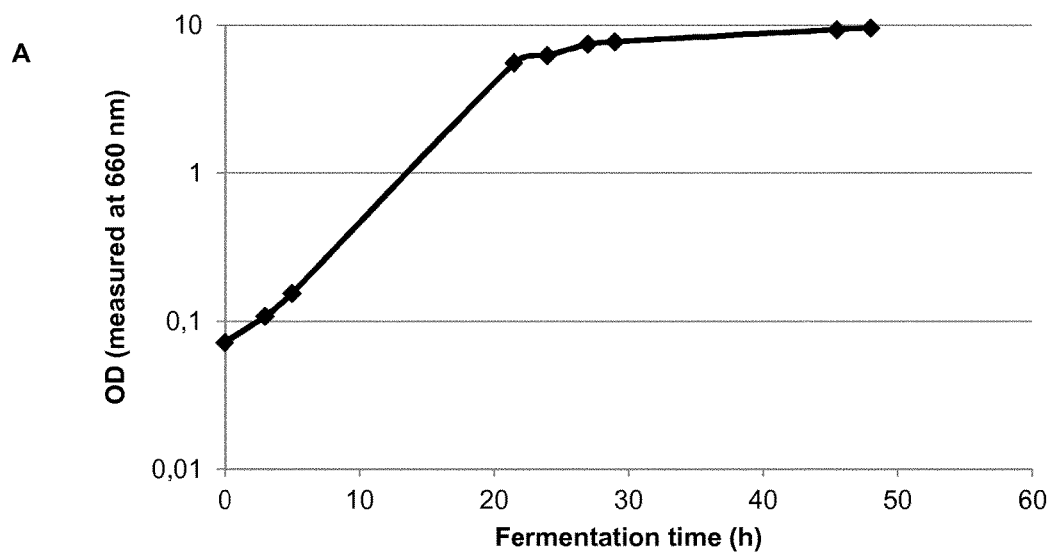
FIG. 5: represents graphs plotting the growth (measured as optical density at 660 nm) over time at 30° C. (A) and at 20° C. (B) of *Saccharomyces bayanus* var. *uvarum* MUCL 55125 incubated with composition B5.
Figure 5:
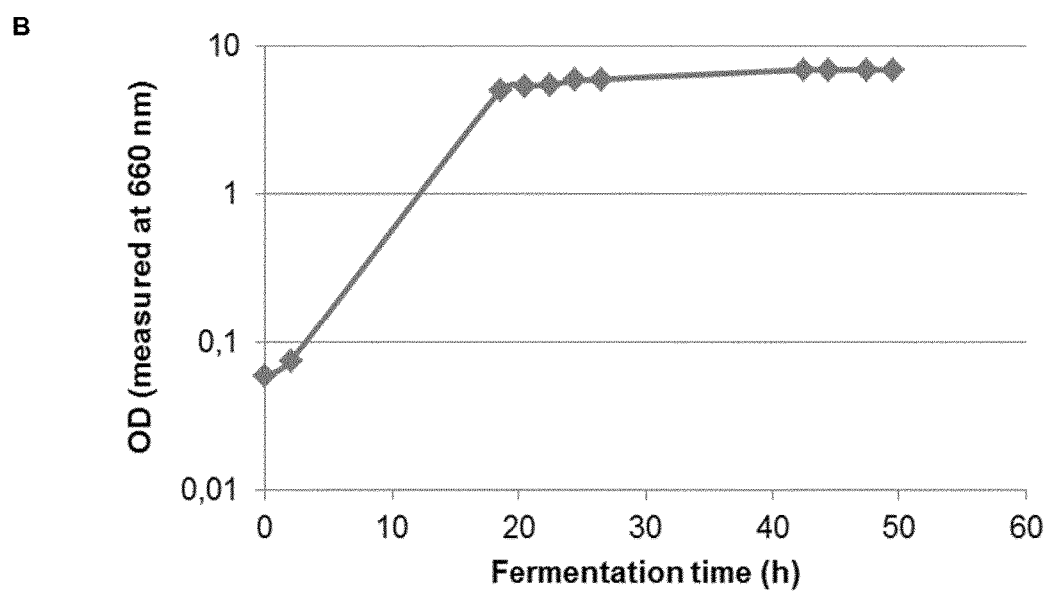
Figure 6:
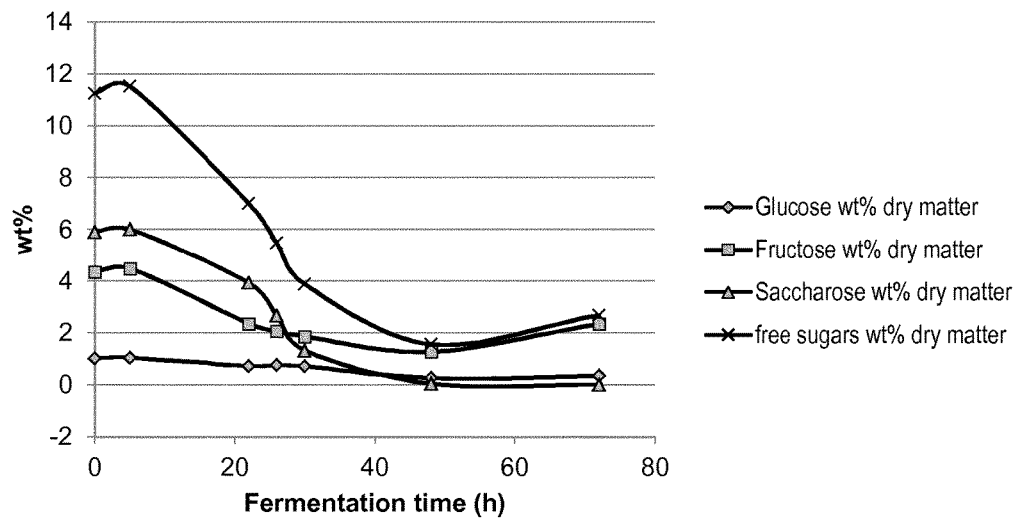
FIG. 6: represents a graph plotting the evolution of free sugars concentration over time at 30° C. of composition B1 incubated with *Saccharomyces cerevisiae* w-34/70. Analyses were performed using HPAEC-PAD (results expressed as wt/wt % based on the total dry matter basis).
Figure 7:
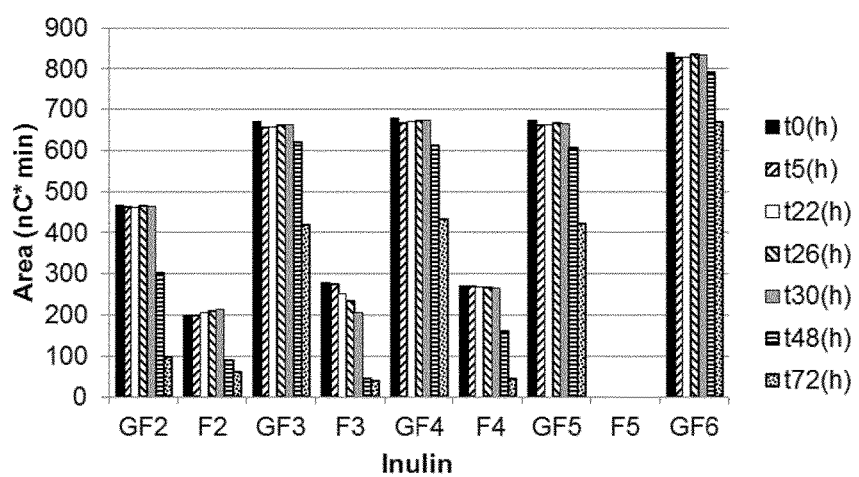
FIG. 7: represents a graph plotting the evolution of peak area of GF2, F2, GF3, F3, GF4, F4, GF5, F5 and GF6 over time at 30° C. of composition B1 incubated with *Saccharomyces cerevisiae* w-34/70. Analyses were performed using HPAEC-PAD (with the area given in nanocoulomb (nC) *retention time (min)—normalized according to the dilution of the composition).
Figure 8:
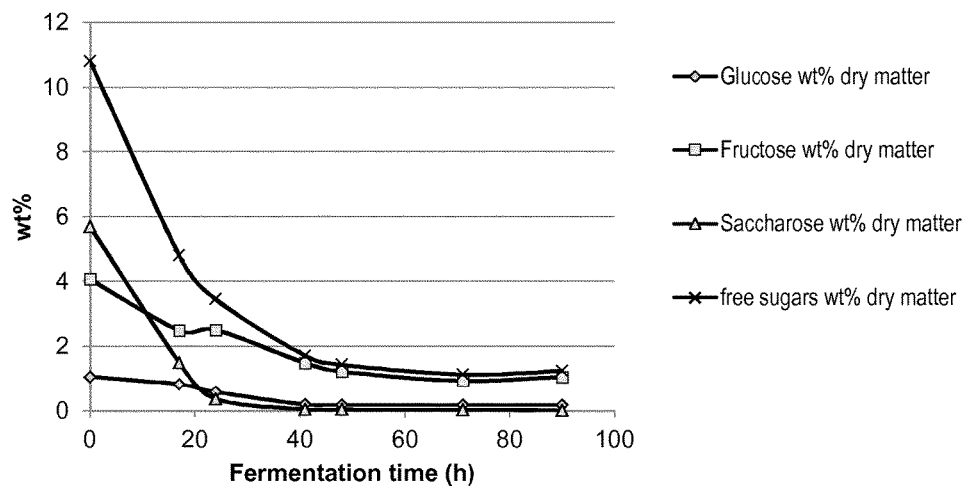
FIG. 8: represents a graph plotting the evolution of free sugars concentration over time at 30° C. of composition B2 incubated with *Kluyveromyces lactis* (CBS 2103). Analyses were performed using HPAEC-PAD (results expressed as wt/wt % based on the total dry matter basis).
Figure 9:
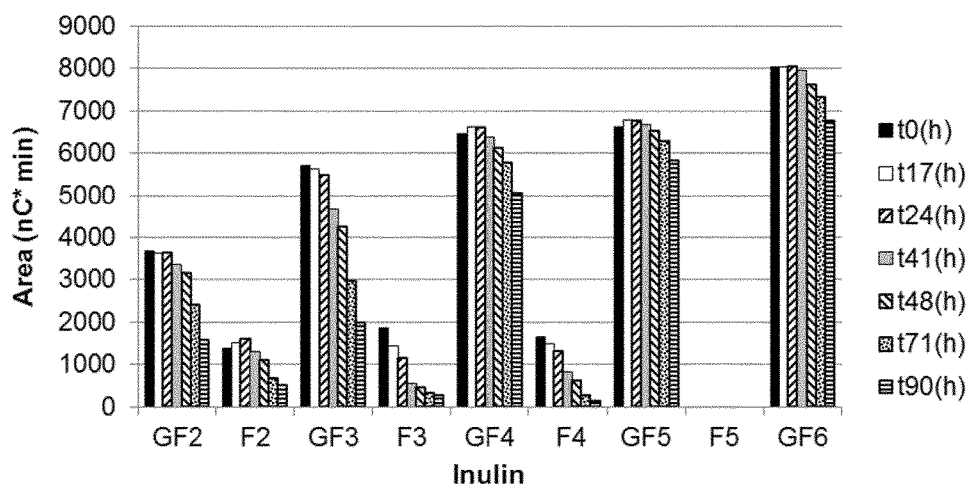
FIG. 9: represents a graph plotting the evolution of peak area of GF2, F2, GF3, F3, GF4, F4, GF5, F5 and GF6 over time at 30° C. of composition B2 incubated with *Kluyveromyces lactis* (CBS 2103). Analyses were performed using HPAEC-PAD (with the area given in nanocoulomb (nC) *retention time (min)—normalized according to the dilution of the composition).
Figure 10:
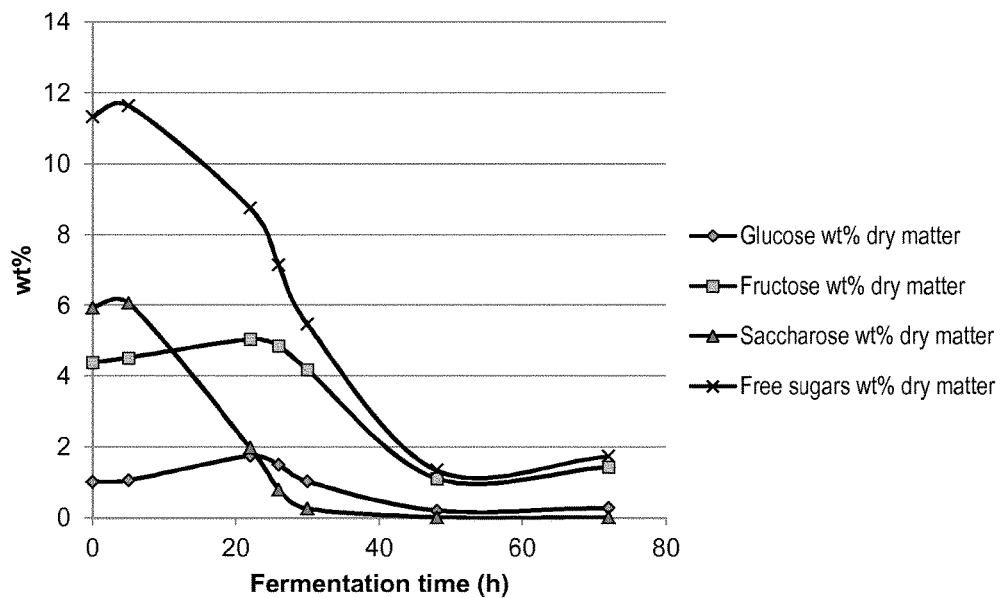
FIG. 10: represents a graph plotting the evolution of free sugars concentration over time at 30° C. of composition B3 incubated with *Saccharomyces bayanus* var. *bayanus* MUCL 31495. Analyses were performed using HPAEC-PAD (results expressed as wt/wt % based on the total dry matter basis).
Figure 11:
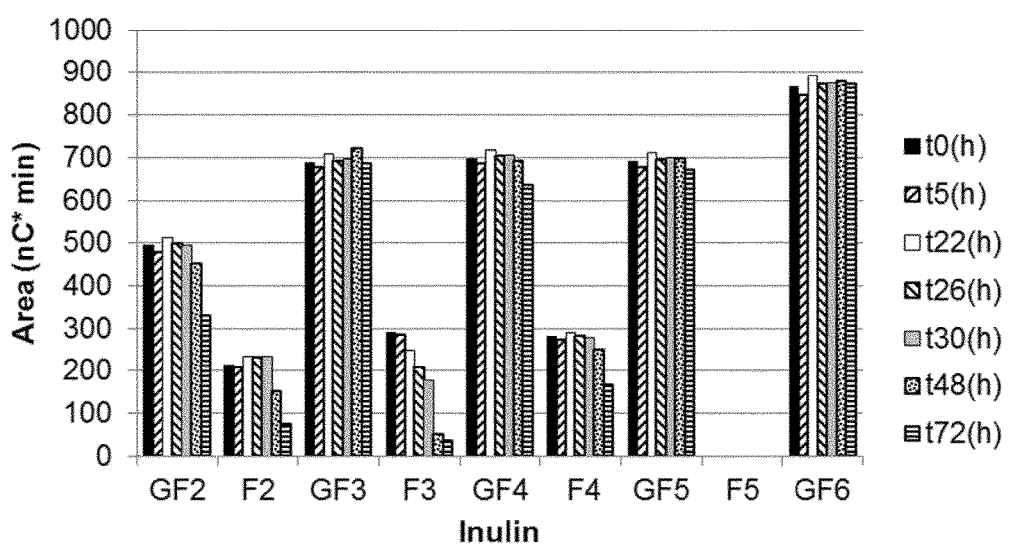
FIG. 11: represents a graph plotting the evolution of peak area of GF2, F2, GF3, F3, GF4, F4, GF5, F5 and GF6 over time at 30° C. of composition B3 incubated with *Saccharomyces bayanus* var. *bayanus* MUCL 31495. Analyses were performed using HPAEC-PAD (with the area given in nanocoulomb (nC)*retention time (min)—normalized according to the dilution of the composition).
Figure 12:
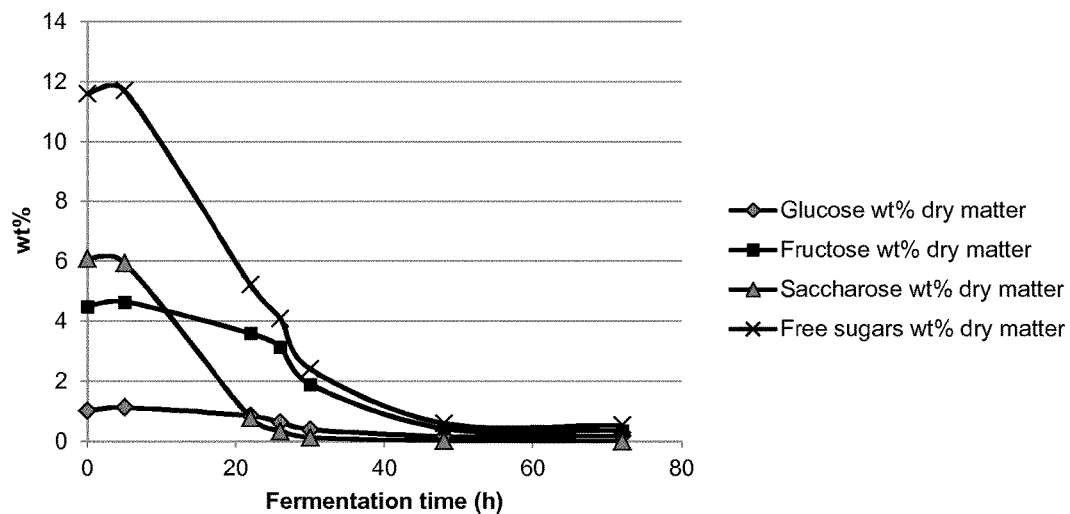
FIG. 12: represents a graph plotting the evolution of free sugars concentration over time at 30° C. of composition B4 incubated with *Saccharomyces bayanus* var. *uvarum* MUCL 31491. Analyses were performed using HPAEC-PAD (results expressed as wt/wt % based on the total dry matter basis).
Figure 13:
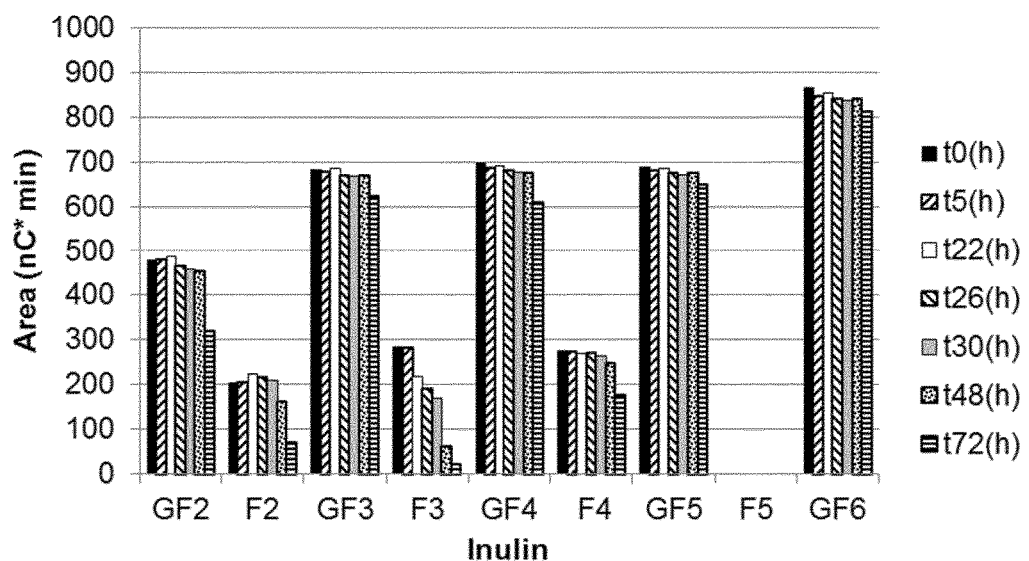
FIG. 13: represents a graph plotting the evolution of peak area of GF2, F2, GF3, F3, GF4, F4, GF5, F5 and GF6 over time at 30° C. of composition B4 incubated with *Saccharomyces bayanus* var. *uvarum* MUCL 31491. Analyses were performed using HPAEC-PAD (with the area given in nanocoulomb (nC)*retention time (min)—normalized according to the dilution of the composition).
Figure 14:
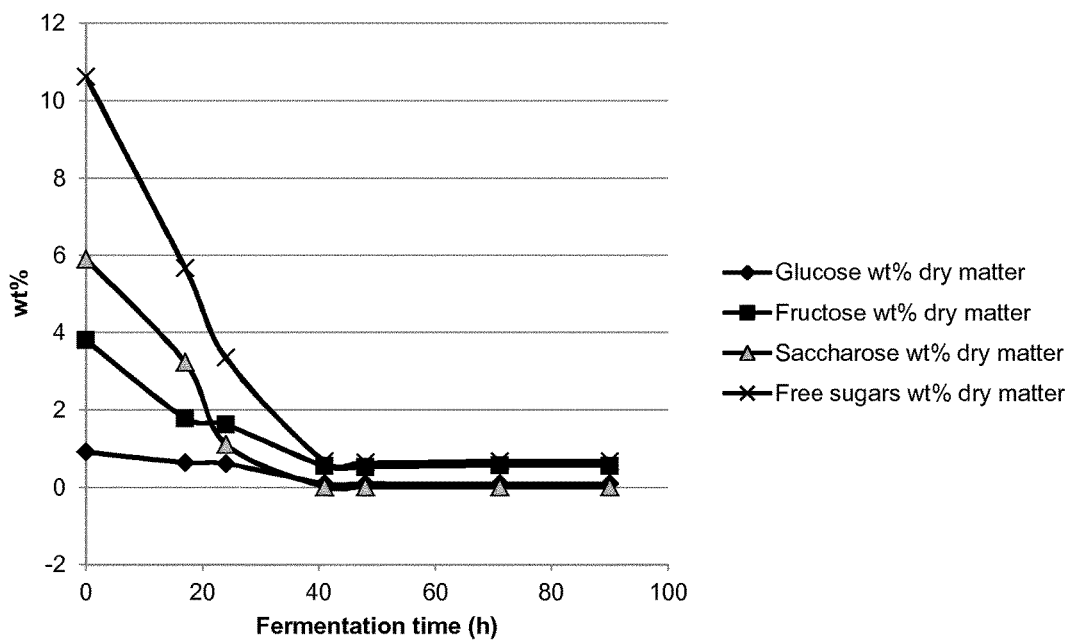
FIG. 14: represents a graph plotting the evolution of free sugars concentration over time at 30° C. of composition B5 incubated with *Saccharomyces bayanus* var. *uvarum* MUCL 55125. Analyses were performed using HPAEC-PAD (results expressed as wt/wt % based on the total dry matter basis).
Figure 15:
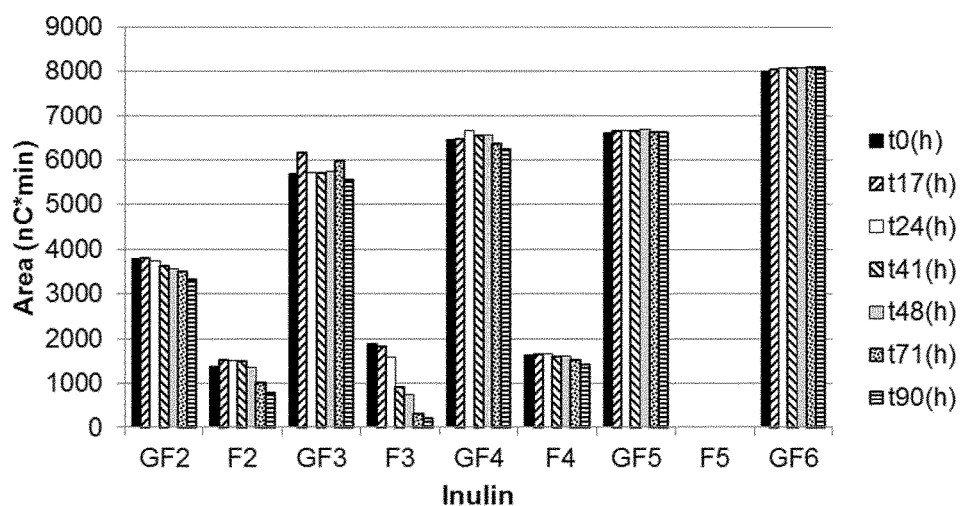
FIG. 15: represents a graph plotting the evolution of peak area of GF2, F2, GF3, F3, GF4, F4, GF5, F5 and GF6 over time at 30° C. of composition B5 incubated with *Saccharomyces bayanus* var. *uvarum* MUCL 55125. Analyses were performed using HPAEC-PAD (with the area given in nanocoulomb (nC)*retention time (min)—normalized according to the dilution of the composition).

FIG. 5 shows the growth (measured as optical density at 660 nm) over time at 30° C. and at 20° C. of Saccharomyces bayanus var. uvarum MUCL 55125 incubated with composition B5 in 250 ml flask.

FIGS. 6, 8, 10, 12 and 14 show the evolution of free sugars concentration over time at 30° C. of composition B1-B5 respectively incubated with Saccharomyces cerevisiae w-34/70, Kluyveromyces lactis CBS 2103, Saccharomyces bayanus var. bayanus MUCL 31495, Saccharomyces bayanus var. uvarum MUCL 31491 and Saccharomyces bayanus var. uvarum MUCL 55125 respectively in 250 ml flask. Analyses were performed using HPAEC-PAD (results expressed as wt/wt % based on the total dry matter basis).

FIGS. 7, 9, 11, 13 and 15 show the evolution of peak area of GF2, F2, GF3, F3, GF4, F4, GF5, F5 and GF6 over time at 30° C. of compositions B1-B5 respectively incubated with Saccharomyces cerevisiae w-34/70, Kluyveromyces lactis CBS 2103, Saccharomyces bayanus var. bayanus MUCL 31495, Saccharomyces bayanus var. uvarum MUCL 31491 and Saccharomyces bayanus var. uvarum MUCL 55125 respectively in 250 ml flask. Analyses were performed using HPAEC-PAD (with the area given in nanocoulomb (nC) *retention time (min)—normalized according to the dilution of the composition).

From FIGS. 6-15, it is clear that the Saccharomyces and Kluyveromyces are good at degrading free sugars. From the figures can be seen that Saccharomyces bayanus var. uvarum MUCL 55125 degrades free sugars faster than Saccharomyces cerevisiae w-34/70, Kluyveromyces lactis CBS 2103, Saccharomyces bayanus var. bayanus MUCL 31495 and Saccharomyces bayanus var. uvarum MUCL 31491, and/or has a higher specificity towards free sugars compared to inulin.

Non-limiting examples of optimal conditions are listed in Table 4. These conditions allow degradation of a maximum amount of free sugars and limited degradation of inulin.

TABLE 4

| Strain | Temperature (° C.) | Duration of fermentation (h) | residual Glucose (wt % of dry matter) | residual Fructose (wt % of dry matter) | residual Sucrose (wt % of dry matter) | Total residual free sugars (wt % of dry matter) | Inulin loss (%) |
|---|---|---|---|---|---|---|---|
| Kluyveromyces lactis CBS 2103 | 30 | 30-35 h | 0-0.5 | 1.5-2.5 | 0-0.5 | 2-3 | 5-10 |
| Saccharomyces | 30 | 30-35 h | 0-0.1 | 0-0.5 | 0 | 0-0.5 | <5 |

TABLE 4-continued

| Strain | Temperature (° C.) | Duration of fermentation (h) | residual Glucose (wt % of dry matter) | residual Fructose (wt % of dry matter) | residual Sucrose (wt % of dry matter) | Total residual free sugars (wt % of dry matter) | Inulin loss (%) |
|---|---|---|---|---|---|---|---|
| bayanus MUCL 55125 | | | | | | | |
| Saccharomyces bayanus MUCL 31491 | 30 | 40-45 h | 0-0.1 | 0-0.5 | 0 | 0-0.5 | <5 |
| Saccharomyces bayanus MUCL 31495 | 30 | 40-45 h | 0-0.5 | 1-2.5 | 0-0.5 | 1-3 | 5-10 |
| Saccharomyces cerevisiae w-34/70 | 30 | 30-35 h | 0-0.5 | 1.5-2.5 | 0-0.5 | 2-3 | 5-10 |

Example 2

Incubation of a Composition Comprising Inulin and Sucrose with *Saccharomyces bayanus* var. *uvarum* MUCL 55125—(Step b)

Example in a 2 L Bioreactor

A yeast extract solution was prepared as follows: 20 g of yeast extract (Merck) were dissolved in 200 ml of demineralized water and sterilized (20 min, 121° C.).

200 g of the sterilized yeast extract solution was added in 2 L bioreactor containing 1800 g of the composition C.

No supplemental aeration was provided. pH of the composition was maintained at a value of 5 using a peristaltic pump providing basic solution as sodium hydroxide 10 mol/L and acid solution as phosphoric acid 30 vol/vol %.

Composition C, complemented with yeast extract, was incubated at a concentration of $10^5$ CFU/ml at 30° C. under a stirring rate of 160 rpm with *Saccharomyces bayanus* var. *uvarum* MUCL 55125.

After 62 h, inulin loss was less than 2%.

Figure 16:
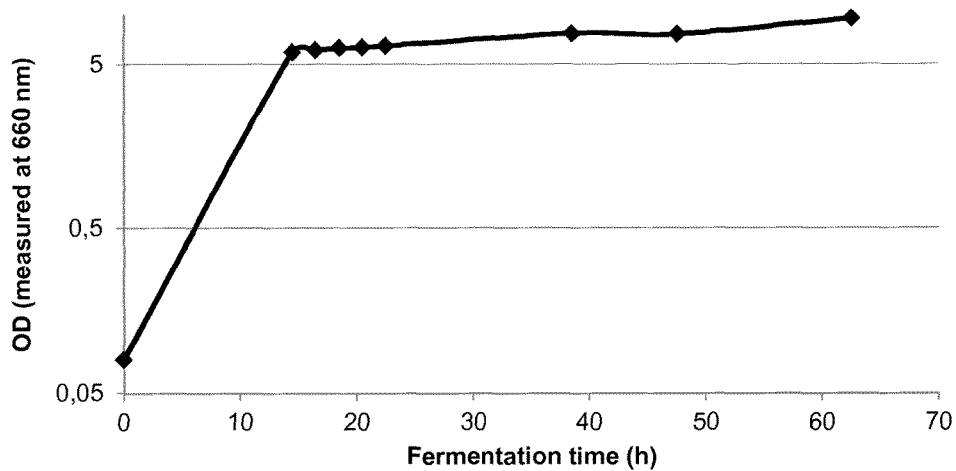
FIG. 16: represents a graph plotting the growth (measured as optical density at 660 nm) over time at 30° C. of *Saccharomyces bayanus* var. *uvarum* MUCL 55125 incubated with composition C.

FIG. 16 shows the growth (measured as optical density) over time at 30° C. of *Saccharomyces bayanus* var. *uvarum* MUCL 55125 incubated with composition C in a 2 L bioreactor.

Figure 17:
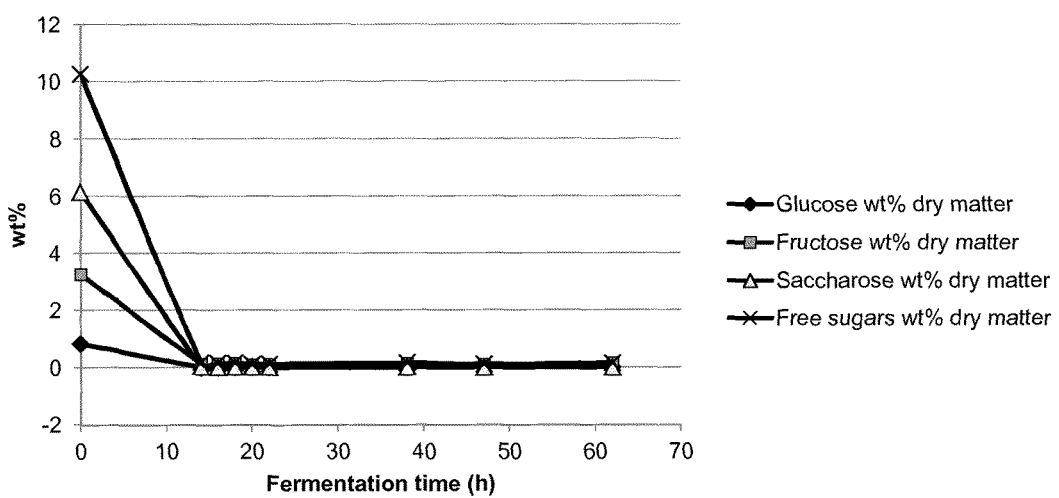
FIG. 17: represents a graph plotting the evolution of free sugars concentration over time at 30° C. of composition C incubated with *Saccharomyces bayanus* var. *uvarum* MUCL 55125. Analyses were performed using HPAEC-PAD (results expressed as wt/wt %).

FIG. 17 shows the evolution of free sugars concentration over time at 30° C. of composition C incubated with *Saccharomyces bayanus* var. *uvarum* MUCL 55125 in a 2 L bioreactor. Analyses were performed using HPAEC-PAD (results expressed as wt/wt % based on the total dry matter basis).

Figure 18:
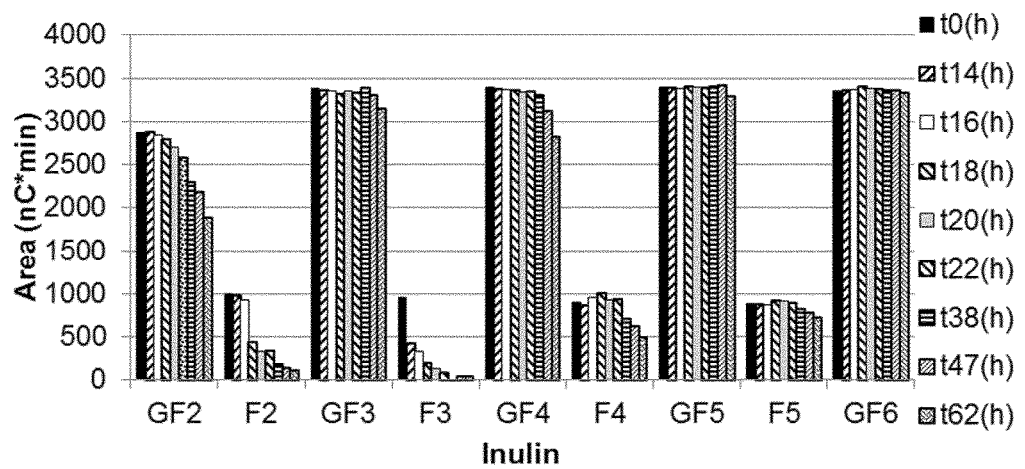
FIG. 18: represents a graph plotting the evolution of peak area of GF2, F2, GF3, F3, GF4, F4, GF5, F5 and GF6 over time at 30° C. of composition C incubated with *Saccharomyces bayanus* var. *uvarum* MUCL 55125. Analyses were performed using HPAEC-PAD (with the area given in nanocoulomb (nC)*retention time (min)—normalized according to the dilution of the composition).

FIG. 18 shows the evolution of peak area of GF2, F2, GF3, F3, GF4, F4, GF5, F5 and GF6 over time at 30° C. of composition C incubated with *Saccharomyces bayanus* var. *uvarum* MUCL 55125 in a 2 L bioreactor. Analyses were performed using HPAEC-PAD (with the area given in nano-coulomb (nC)*retention time (min)—normalized according to the dilution of the composition).

Example in a 60 L Barrel 40 g of yeast extract (Merck) were dissolved in 100 ml of demineralized water. Then, the solution was sterilized (20 min, 121° C.) and added to 40 kg of composition D.

No supplemental aeration was provided. The pH was not controlled.

Composition D, complemented with yeast extract, was inoculated at a concentration of $10^5$ CFU/ml at 20° C. without stirring with *Saccharomyces bayanus* var. *uvarum* MUCL 55125.

Figure 19:
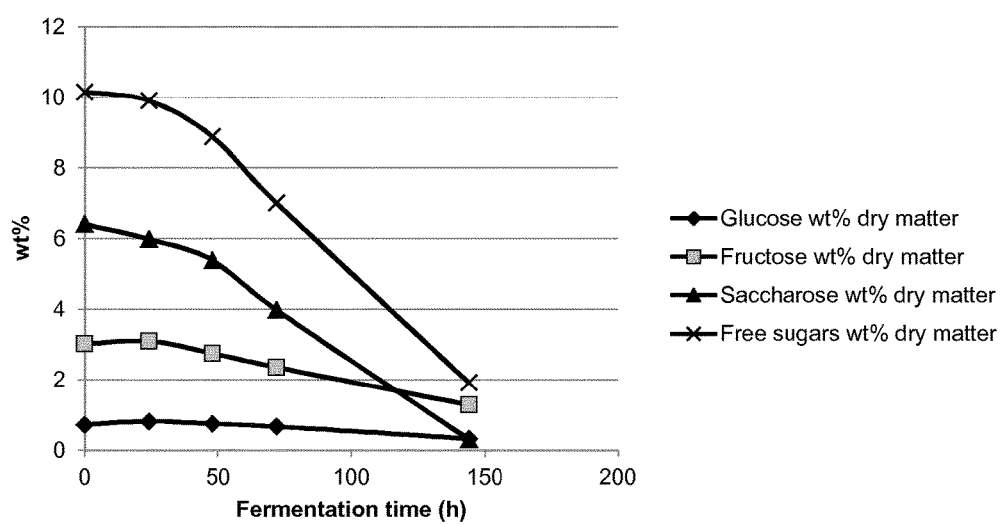
FIG. 19: represents a graph plotting the evolution of free sugars concentration over time at 20° C. of composition D incubated with *Saccharomyces bayanus* var. *uvarum* MUCL 55125. Analyses were performed using HPAEC-PAD (results expressed as wt/wt %).

FIG. 19 shows the evolution of free sugars concentration over time at 20° C. of composition D incubated with *Saccharomyces bayanus* var. *uvarum* MUCL 55125 in a 60 L barrel. Analyses were performed using HPAEC-PAD (results expressed as wt/wt % based on the total dry matter basis).

Figure 20:
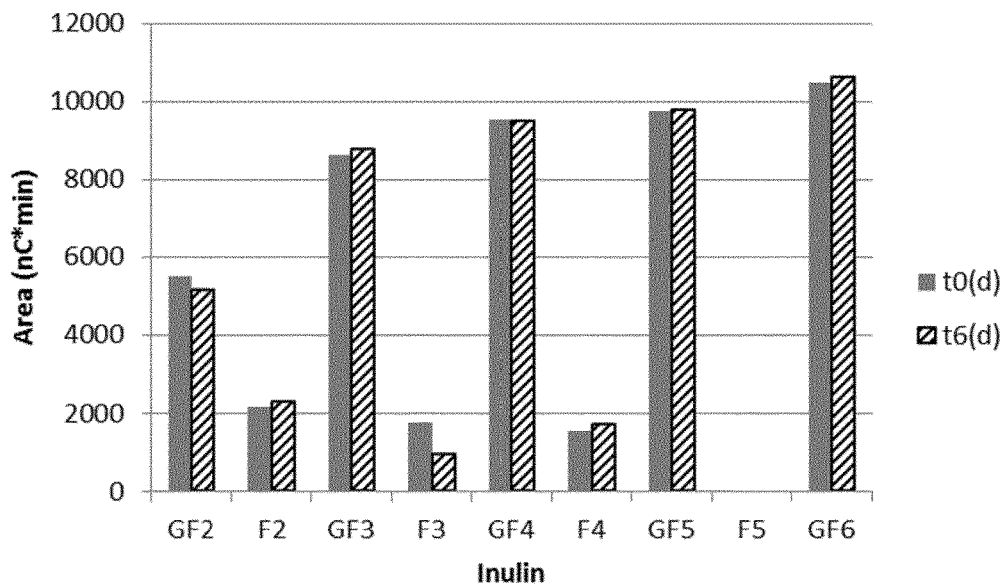
FIG. 20: represents a graph plotting the evolution of peak area of GF2, F2, GF3, F3, GF4, F4, GF5, F5 and GF6 over time at 20° C. of composition D incubated with *Saccharomyces bayanus* var. *uvarum* MUCL 55125. Analyses were performed using HPAEC-PAD (with the area given in nanocoulomb (nC)*retention time (min)—normalized according to the dilution of the composition).

FIG. 20 shows the evolution of peak area of GF2, F2, GF3, F3, GF4, F4, GF5, F5 and GF6 over time at 20° C. of composition D incubated with *Saccharomyces bayanus* var. *uvarum* MUCL 55125 in a 60 L barrel. Analyses were performed using HPAEC-PAD (with the area given in nano-coulomb (nC)*retention time (min)—normalized according to the dilution of the composition).

After 150 h, inulin loss for composition D was less than 2%.

40 g of yeast extract (Merck) were dissolved in 100 ml of demineralized water. Then, the solution was sterilized (20 min, 121° C.) and added to 40 kg of composition E.

No supplemental aeration was provided. The pH was not controlled.

Composition E, complemented with yeast extract, was inoculated at a concentration of $10^5$ CFU/ml at 20° C. without stirring with *Saccharomyces bayanus* var. *uvarum* MUCL 55125.

Figure 21:
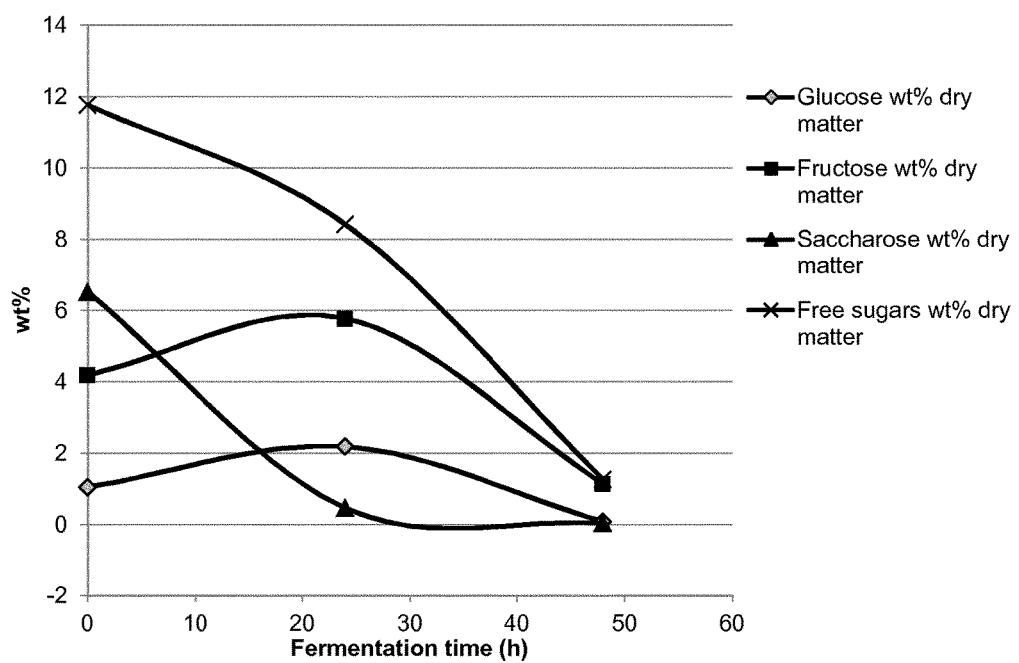
FIG. 21: represents a graph plotting the evolution of free sugars concentration over time at 20° C. of composition E incubated with *Saccharomyces bayanus* var. *uvarum* MUCL 55125. Analyses were performed using HPAEC-PAD (results expressed as wt/wt %).

FIG. 21 shows the evolution of free sugars concentration over time at 20° C. of composition E incubated with *Saccharomyces bayanus* var. *uvarum* MUCL 55125 in a 60 L barrel. Analyses were performed using HPAEC-PAD (results expressed as wt/wt %).

Figure 22:
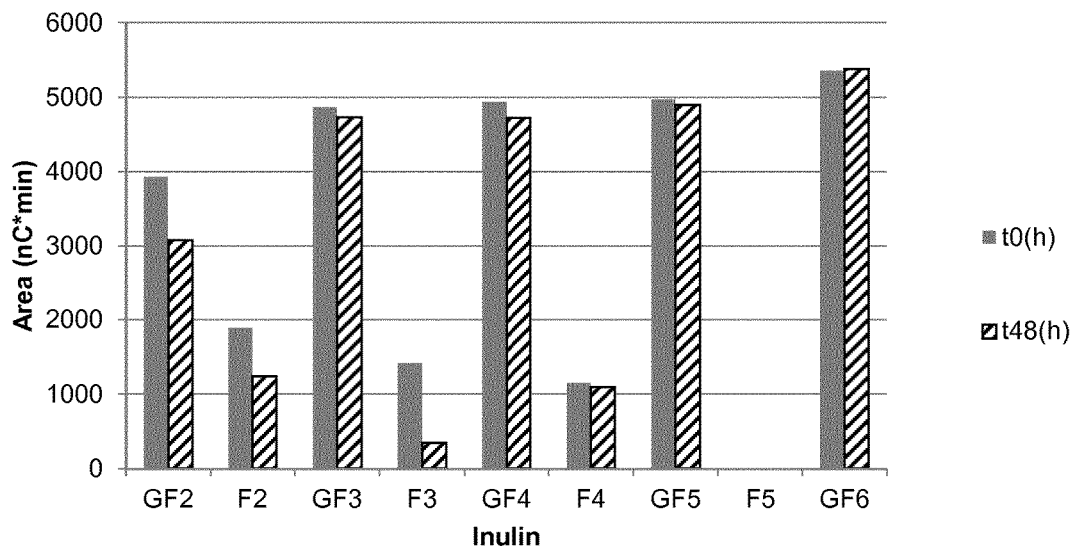
FIG. 22: represents a graph plotting the evolution of peak area of GF2, F2, GF3, F3, GF4, F4, GF5, F5 and GF6 over time at 20° C. of composition E incubated with *Saccharomyces bayanus* var. *uvarum* MUCL 55125. Analyses were performed using HPAEC-PAD (with the area given in nanocoulomb (nC)*retention time (min)—normalized according to the dilution of the composition).

FIG. 22 shows the evolution of peak area of GF2, F2, GF3, F3, GF4, F4, GF5, F5 and GF6 over time at 20° C. of composition E incubated with *Saccharomyces bayanus* var. *uvarum* MUCL 55125 in a 60 L barrel. Analyses were performed using HPAEC-PAD (with the area given in nano-coulomb (nC)*retention time (min)–normalized according to the dilution of the composition).

After 50 h inulin loss for composition E was less than 4%.

Example 3

Incubation of a Composition Comprising Inulin and Sucrose, with *Saccharomyces bayanus* var. *uvarum* (MUCL 55125)—Step (b)

2 kg of composition A1 were inoculated at a concentration of $10^5$ CFU/ml with *Saccharomyces bayanus* var. *uvarum* MUCL 55125 and incubated at different temperatures (20° C. and 30° C.) with a stirring rate of 160 rpm in a 2 L bioreactor.

Composition A1 was not sterilized. No supplemental nitrogen source and aeration were added. pH of the composition was maintained at a value of 5 using peristaltic pump providing basic solution as sodium hydroxide 10 mol/l and acid solution as phosphoric acid 30 vol/vol %.

Figure 23:
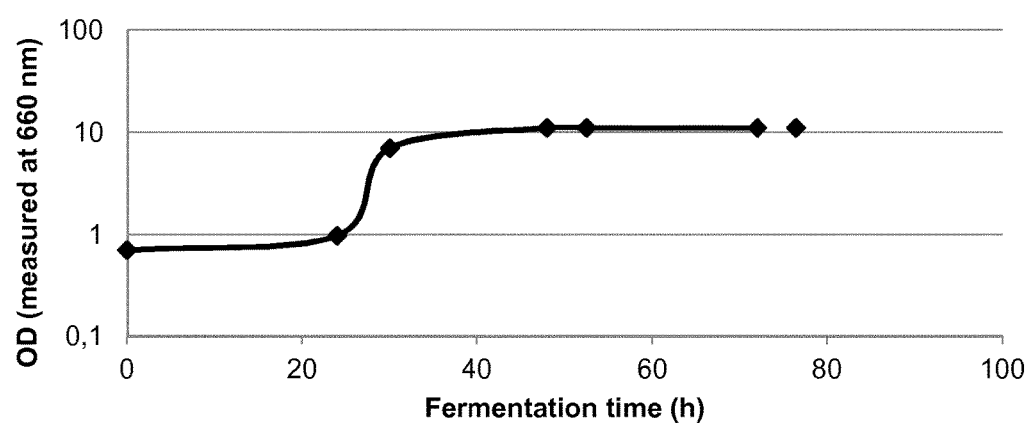
FIG. 23: represents a graph plotting the growth (measured as optical density at 660 nm) over time at 30° C. of *Saccharomyces bayanus* var. *uvarum* MUCL 55125 incubated with composition A1.

FIG. 23 shows the growth at 30° C. (measured as optical density) over time of *Saccharomyces bayanus* var. *uvarum* MUCL 55125 incubated with the composition A1 in a 2 L bioreactor.

Figure 24:
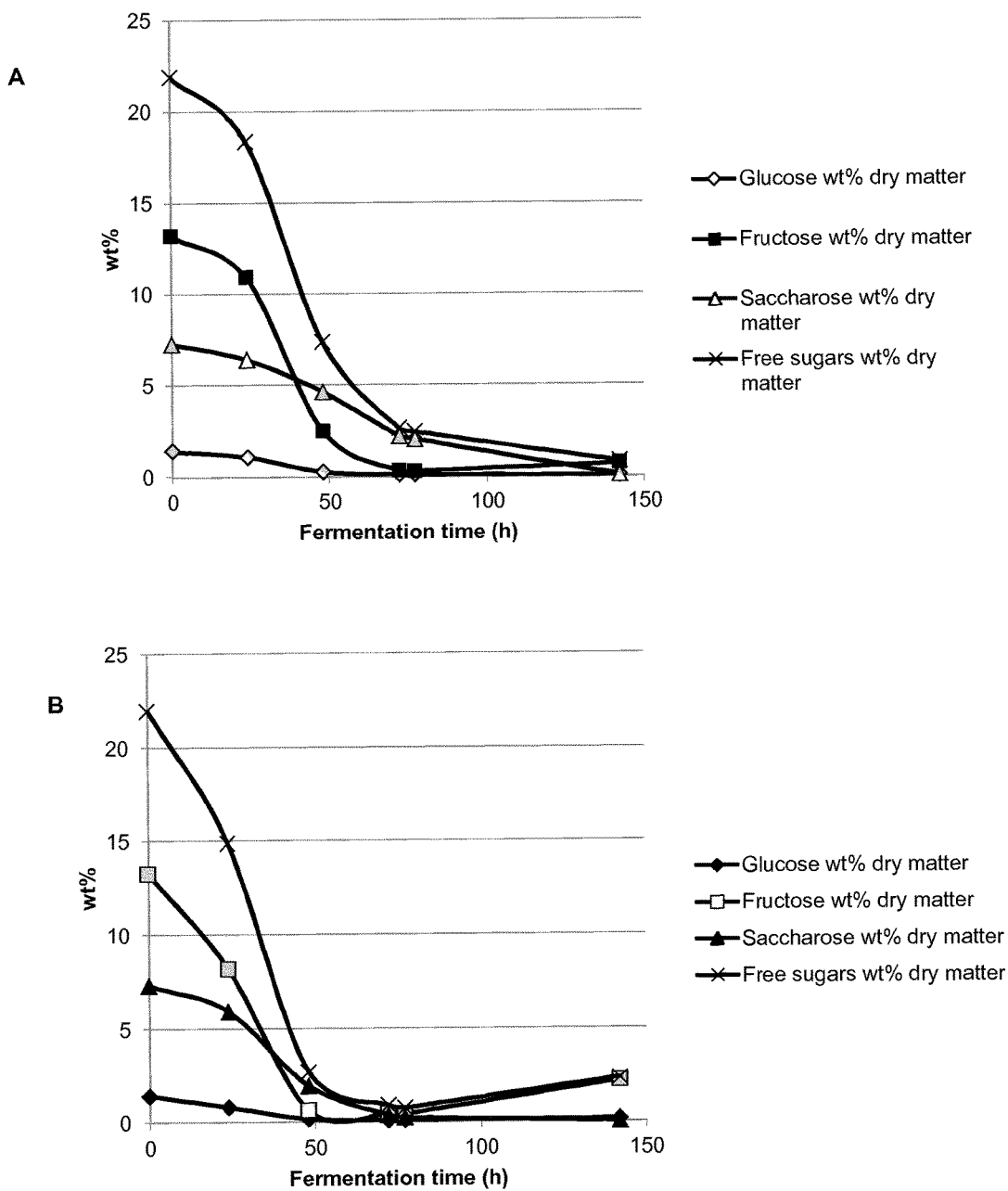
FIG. 24: represents graphs plotting the evolution of free sugars concentration over time at 20° C. (A) and at 30° C. (B) of composition A1 incubated with *Saccharomyces bayanus* var. *uvarum* MUCL 55125. Analyses were performed using HPAEC-PAD (results expressed as wt/wt %).

FIG. 24 shows the evolution of free sugars concentration over time at 20° C. (A) and at 30° C. (B) of the composition A1 incubated with *Saccharomyces bayanus* var. *uvarum* MUCL 55125 in 2 L bioreactor. Analyses were performed using HPAEC-PAD (results expressed as w/w % based on the total dry matter basis).

Figure 25:
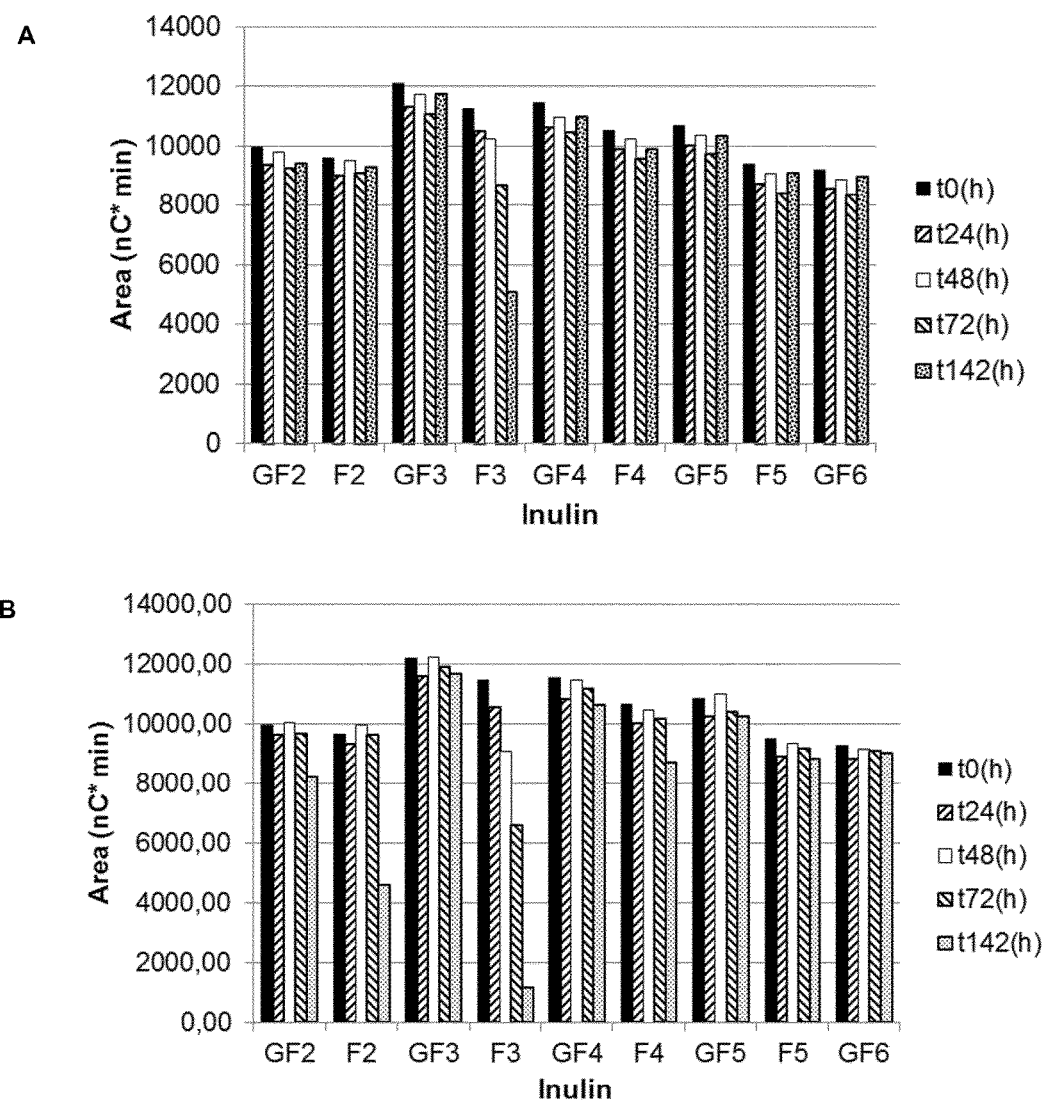
FIG. 25: represents graphs plotting the evolution of peak area of GF2, F2, GF3, F3, GF4, F4, GF5, F5 and GF6 over time at 20° C. (A) and 30° C. (B) of composition A1 incubated with *Saccharomyces bayanus* var. *uvarum* MUCL 55125. Analyses were performed using HPAEC-PAD (with the area given in nanocoulomb (nC)*retention time (min)—normalized according to the dilution of the composition).

FIG. 25 shows the evolution of peak area of GF2, F2, GF3, F3, GF4, F4, GF5, F5 and GF6 over time at 20° C. (A) and 30° C. (B) of the composition A1 incubated with *Saccharomyces bayanus* var. *uvarum* MUCL 55125 in a 2 L bioreactor. Analyses were performed using HPAEC-PAD (with the area given in nanocoulomb (nC)*retention time (min)—normalized according to the dilution of the composition).

Table 5 shows the list and concentration of by-products isolated from composition A1 before and after incubation with *Saccharomyces bayanus* var. *uvarum* MUCL 55125 at 20° C.

TABLE 5

Composition A incubated at 20° C.

|  | Before incubation ml/l | After incubation ml/l |
|---|---|---|
| Acetaldehyde | 0.0042 | 0.0155 |
| Ethyl acetate | 0.00052 | 0.0528 |
| Propanol | 0 | 0.0231 |
| Isobutanol | 0 | 0.0196 |
| Isoamylalcool | 0.00266 | 0.0891 |
| Ethanol | 0 | 46 |

|  | g/l | g/l |
|---|---|---|
| Citrate | 5.8 | 4.715 |
| Pyruvate | 0.075 | 0.27 |
| Malate | 4.85 | 5.64 |
| Succinate | 4.78 | 2.51 |
| Lactate | 1.63 | 1.46 |
| Acetate | 3.163 | 3.46 |
| Propionate | 0 | 0 |
| Butyrate | 0 | 0 |

It can be seen from the results of Table 5 that incubation with *Saccharomyces bayanus* var. *uvarum* MUCL 55125 mainly ethanol is produced as free-sugars degradation products.

Example 4

Incubation of a Composition Comprising Inulin and Sucrose, with *Saccharomyces bayanus* var. *uvarum* MUCL 55125, at 4° C.—Step (b)

1 kg of composition A2 were inoculated at a concentration of $10^5$ CFU/ml with *Saccharomyces bayanus* var. *uvarum* MUCL 55125 and incubated at 4° C. in a 1 L flask with a stirring rate of 110 rpm. The composition A2 was not sterilized. No supplemental nitrogen source and aeration were added. The pH was not controlled.

Figure 26:
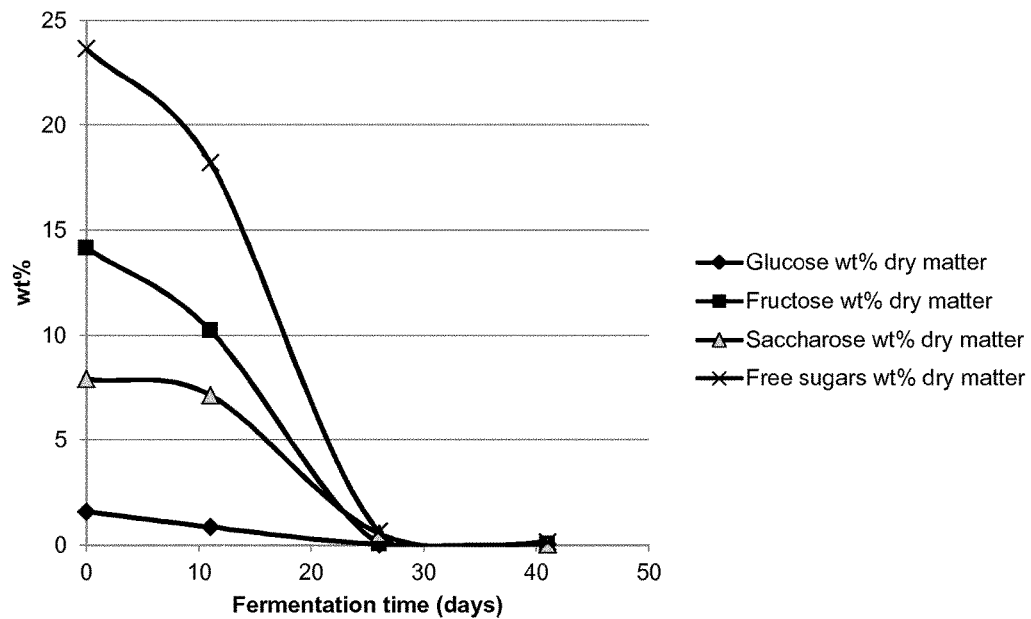
FIG. 26: represents a graph plotting the evolution of free sugars concentration over time at 4° C. of composition A2 incubated with *Saccharomyces bayanus* var. *uvarum* MUCL 55125. Analyses were performed using HPAEC-PAD (results expressed as wt/wt %).

FIG. 26 shows the evolution of free sugars concentration over time at 4° C. of the composition A2 incubated with *Saccharomyces bayanus* var. *uvarum* MUCL 55125 in 1 L flask. Analyses were performed using HPAEC-PAD (results expressed as wt/wt % based on the total dry matter basis).

Figure 27:
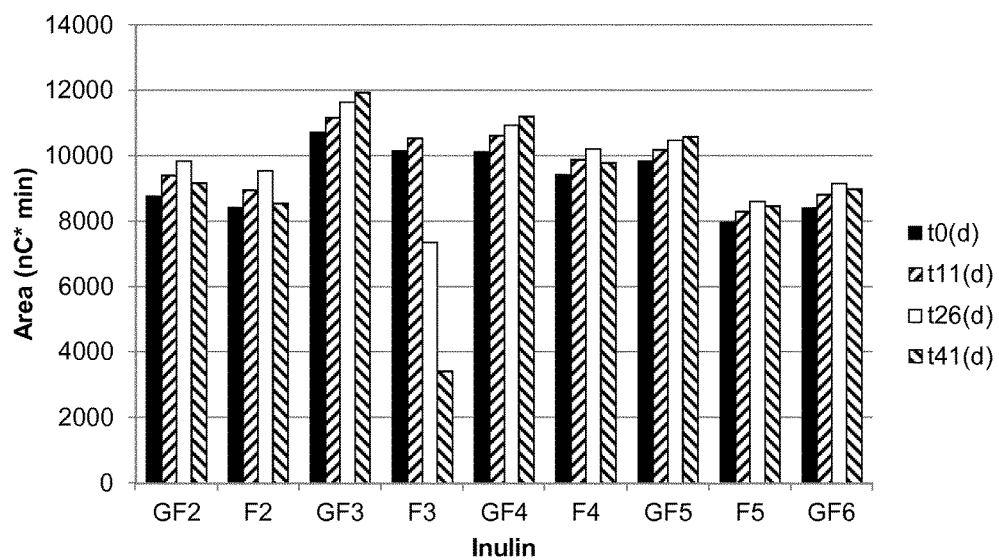
FIG. 27: represents a graph plotting the evolution of peak area of GF2, F2, GF3, F3, GF4, F4, GF5, F5 and GF6 over time at 4° C. of composition A2 incubated with *Saccharomyces bayanus* var. *uvarum* MUCL 55125. Analyses were performed using HPAEC-PAD (with the area given in nanocoulomb (nC)*retention time (min)—normalized according to the dilution of the composition).

FIG. 27 shows the evolution of peak area of GF2, F2, GF3, F3, GF4, F4, GF5, F5 and GF6 over time at 4° C. of the composition A2 incubated with *Saccharomyces bayanus* var. *uvarum* MUCL 55125 in 1 L flask. Analyses were performed using HPAEC-PAD (with the area given in nanocoulomb (nC)*retention time (min)–normalized according to the dilution of the composition).

Even at low temperature, *Saccharomyces bayanus* var. *uvarum* MUCL 55125 is active to accomplish adequate free sugars degradation (although slower) without significant inulin degradation, compared to experiments performed at room temperature (FIGS. 24 and 25).

Example 5

Study of *Saccharomyces bayanus* var. *uvarum* MUCL 55125 Metabolism with Aeration—Step (b)

2 kg of composition A3 were inoculated with *Saccharomyces bayanus* var. *uvarum* MUCL 55125 at a concentration of $10^5$ CFU/ml and incubated at 25° C. in 2 L bioreactor with a stirring rate of 160 rpm and an aeration rate of 1 L/min.

The composition A3 was not sterilized. No supplemental nitrogen source was added. pH of the composition A3 was maintained at a value of 5 using peristaltic pump providing basic solution as sodium hydroxide 10 mol/l and acid solution as phosphoric acid 30 vol/vol %.

Figure 28:
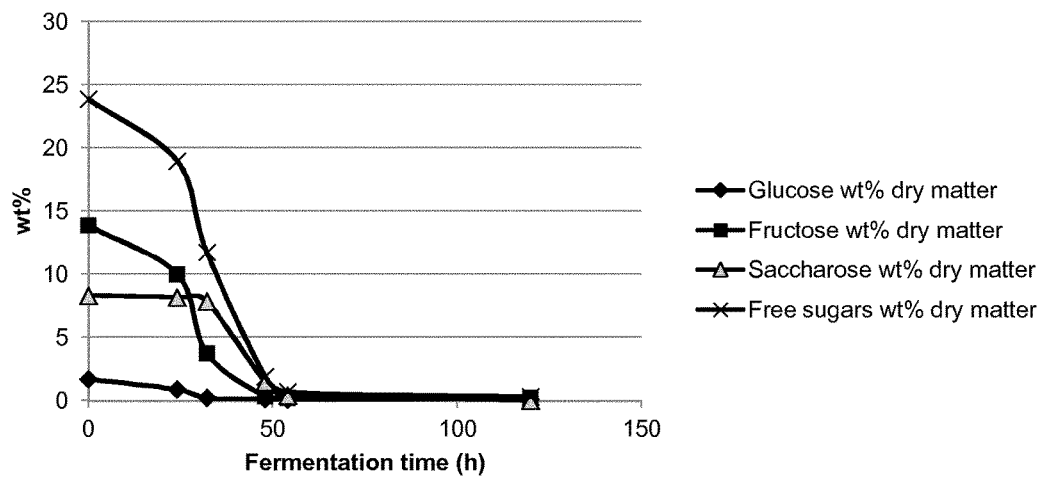
FIG. 28: represents a graph plotting the evolution of free sugars concentration over time at 25° C. with aeration of composition A3 incubated with *Saccharomyces bayanus* var. *uvarum* MUCL 55125. Analyses were performed using HPAEC-PAD (results expressed as wt/wt %).

FIG. 28 shows the evolution of free sugars concentration over time at 25° C. with aeration of the composition A3 incubated with *Saccharomyces bayanus* var. *uvarum* MUCL 55125 in 2 L bioreactor. Analyses were performed using HPAEC-PAD (results expressed as wt/wt % based on the total dry matter basis).

Figure 29:
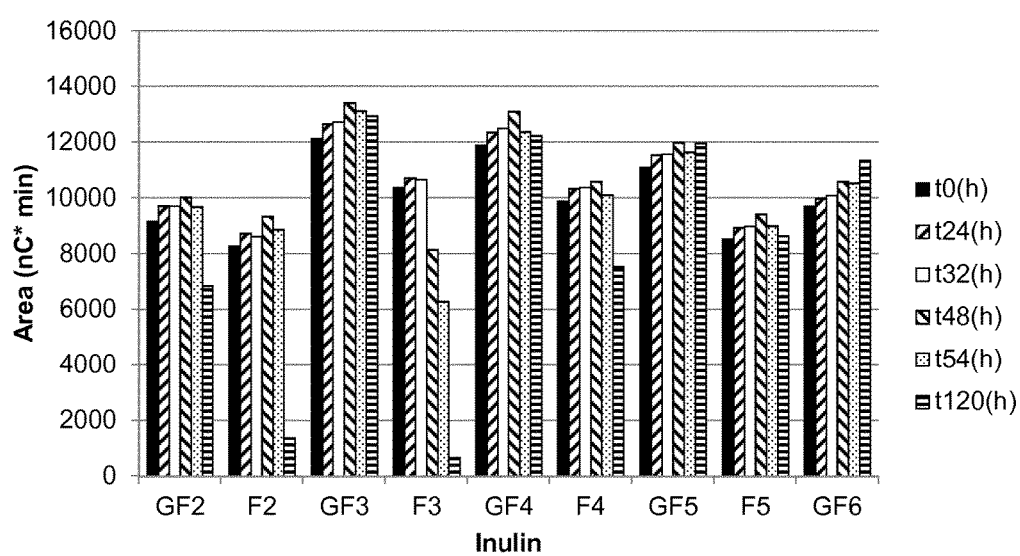
FIG. 29 represents a graph plotting the evolution of peak area of GF2, F2, GF3, F3, GF4, F4, GF5, F5 and GF6 over time at 25° C. with aeration of composition A3 incubated with *Saccharomyces bayanus* var. *uvarum* MUCL 55125. Analyses were performed using HPAEC-PAD (with the area given in nanocoulomb (nC)*retention time (min)—normalized according to the dilution of the composition).

FIG. 29 shows the evolution of peak area of GF2, F2, GF3, F3, GF4, F4, GF5, F5 and GF6 over time at 25° C. with aeration of the composition A3 incubated with *Saccharomyces bayanus* var. *uvarum* MUCL 55125 in 2 L bioreactor. Analyses were performed using HPAEC-PAD (with the area given in nanocoulomb (nC)*retention time (min)–normalized according to the dilution of the composition).

Aeration stimulates fermentation of free sugars. Indeed, the degradation of free sugars by the yeast was much faster compared to fermentation that occurs without aeration (FIGS. 24 and 25).

Example 6

Comparative: Incubation of a Composition Comprising Inulin and Sucrose, with *Rhodotorula dairenensis* CBS 7294 (Step b)

A yeast extract solution was prepared as follows: 10 g of yeast extract (Merck) were dissolved in 100 ml of demineralized water. Then the solution was sterilized (20 min, 121° C.).

10 g of the sterilized yeast extract solution were added to 90 g composition B6. No supplemental aeration was provided.

Figure 30:
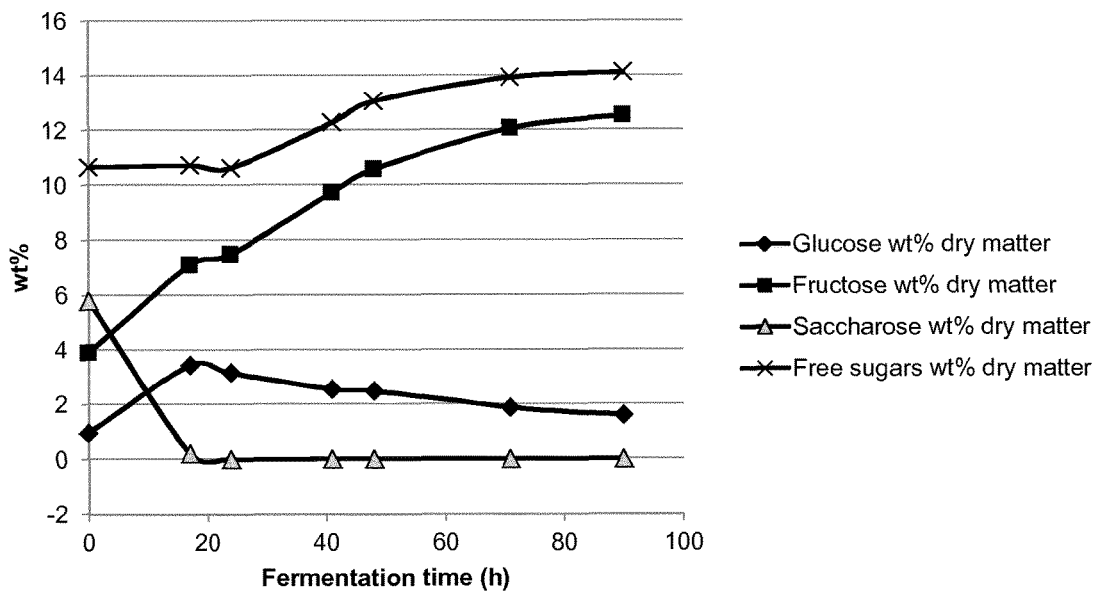
FIG. 30 represents a graph plotting the evolution of free sugars concentration over time at 30° C. of composition B6 incubated with *Rhodotolula dairenensis* (CBS 7294). Analyses were performed using HPAEC-PAD (results expressed as wt/wt %).

Composition B6, complemented with yeast extract, was inoculated with *Rhodotorula dairenensis* CBS 7294 (from CBS-KNAW fungal biodiversity center, Utrecht NL) at a concentration of $10^5$ CFU/ml and incubated at 30° C. with a stirring rate of 160 rpm FIG. 30 shows the evolution of free sugars concentration over time at 30° C. of the composition B6 incubated with

*Rhodotolula dairenensis* CBS 7294 in 250 ml flask. Analyses were performed using HPAEC-PAD (results expressed as wt/wt % based on the total dry matter basis).

Figure 31:
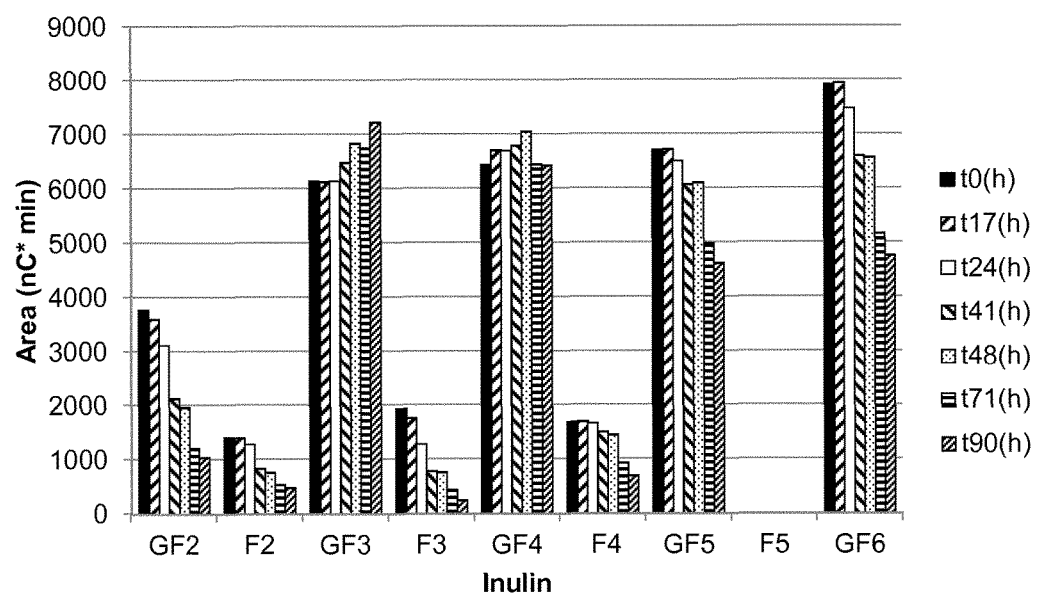
FIG. 31 represents a graph plotting the evolution of peak area of GF2, F2, GF3, F3, GF4, F4, GF5, F5 and GF6 over time at 30° C. of composition B6 incubated with *Rhodotolula dairenensis* (CBS 7294). Analyses were performed using HPAEC-PAD (with the area given in nanocoulomb (nC)*retention time (min)—normalized according to the dilution of the composition).

FIG. 31 shows the evolution of peak area of GF2, F2, GF3, F3, GF4, F4, GF5, F5 and GF6 over time at 30° C. of composition B6 incubated with *Rhodotolula dairenensis* CBS 7294 in 250 ml flask. Analyses were performed using HPAEC-PAD (with the area given in nanocoulomb (nC) *retention time (min)–normalized according to the dilution of the composition).

From FIGS. 30-31 and 17-18, it is clear that *Saccharomyces bayanus* var. *uvarum* MUCL 55125 degrades all the tested free sugars while *Rhodotolula dairenensis* CBS 7294 generates more free sugars. *Saccharomyces bayanus* var. *uvarum* MUCL 55125 clearly has a higher specificity towards free sugars compared to inulin.

Example 7

Comparative: Incubation of a Composition Comprising Inulin and Sucrose, with *Aureobasidium Pullulans* CBS 621.80—(Step b)

A yeast extract solution was prepared as follows: 10 g of yeast extract (Merck) were dissolved in 100 ml of demineralized water. Then the solution was sterilized (20 min, 121° C.).

10 g of the sterilized yeast extract solution were added to 90 g composition B7. No supplemental aeration was provided.

Composition B7, complemented with yeast extract, was inoculated with *Aureobasidium Pullulans* CBS621.80 (obtained from CBS-KNAW fungal biodiversity center, Utrecht NL) at a optical density (OD at 660 nm) of 0.1 and incubated at 30° C. with a stirring rate of 160 rpm.

Figure 32:
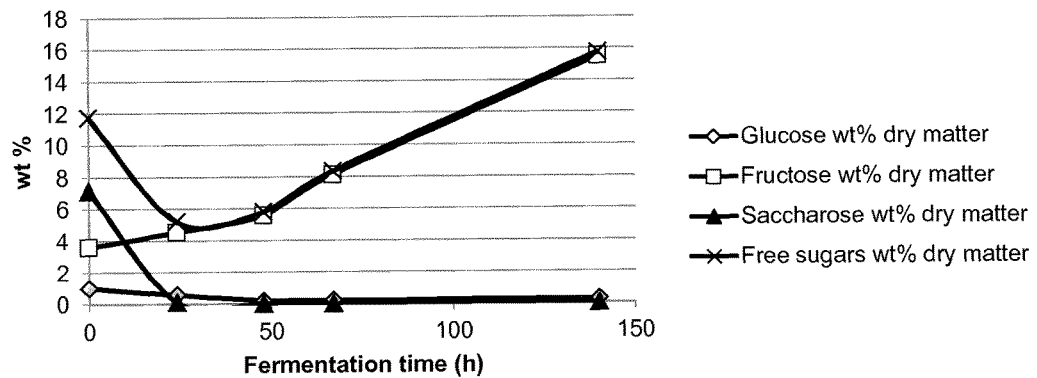
FIG. 32 represents a graph plotting the evolution of free sugars concentration over time at 30° C. of composition B7 incubated with *Aureobasidium Pullulans* (CBS621.80). Analyses were performed using HPAEC-PAD (results expressed as wt/wt %).

FIG. 32 shows the evolution of free sugars concentration over time at 30° C. of the composition B7 incubated with *Aureobasidium Pullulans* CBS 621.80. Analyses were performed using HPAEC-PAD (results expressed as wt/wt % based on the total dry matter basis).

Figure 33:
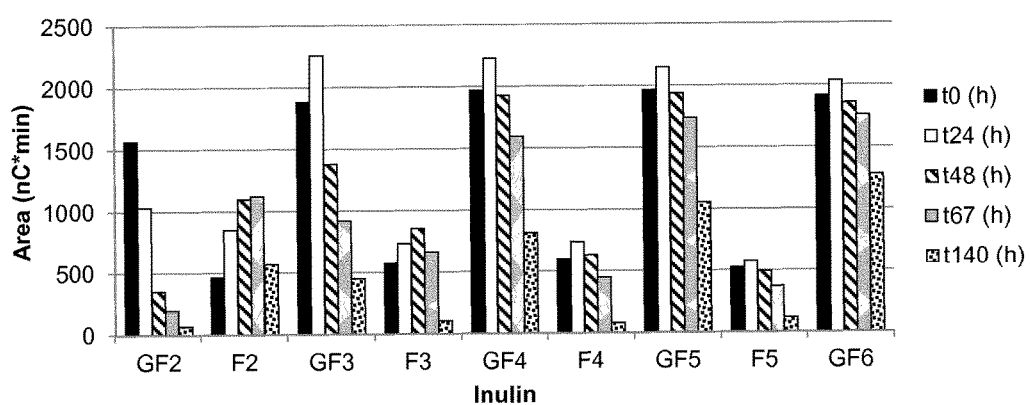
FIG. 33 represents a graph plotting the evolution of peak area of GF2, F2, GF3, F3, GF4, F4, GF5, F5 and GF6 over time at 30° C. of composition B7 incubated with *Aureobasidium Pullulans* (CBS 621.80). Analyses were performed using HPAEC-PAD (with the area given in nanocoulomb (nC)*retention time (min)—normalized according to the dilution of the composition).

FIG. 33 shows the evolution of peak area of GF2, F2, GF3, F3, GF4, F4, GF5, F5 and GF6 over time at 30° C. of composition B7 incubated with *Aureobasidium Pullulans* CBS 621.80. Analyses were performed using HPAEC-PAD (with the area given in nanocoulomb (nC)*retention time (min)—normalized according to the dilution of the composition).

From FIGS. 32-33 and 17-18, it is clear that *Saccharomyces bayanus* var. *uvarum*(MUCL 55125) degrades all the tested free sugars while *Aureobasidium Pullulans* CBS 621.80 generates more free sugars. *Saccharomyces bayanus* var. *uvarum* MUCL 55125clearly has a higher specificity towards free sugars compared to inulin.

Example 8

Incubation of a Composition Comprising Inulin and Sucrose, with *Saccharomyces bayanus* var. *uvarum* MUCL 55125—(Step b)

40 kg of composition F in a barrel of 60 L were inoculated at a concentration of $10^5$ CFU/ml at 30° C. without stirring with *Saccharomyces bayanus* var. *uvarum* MUCL 55125.

No supplemental aeration was provided. The pH was not controlled.

Figure 34:
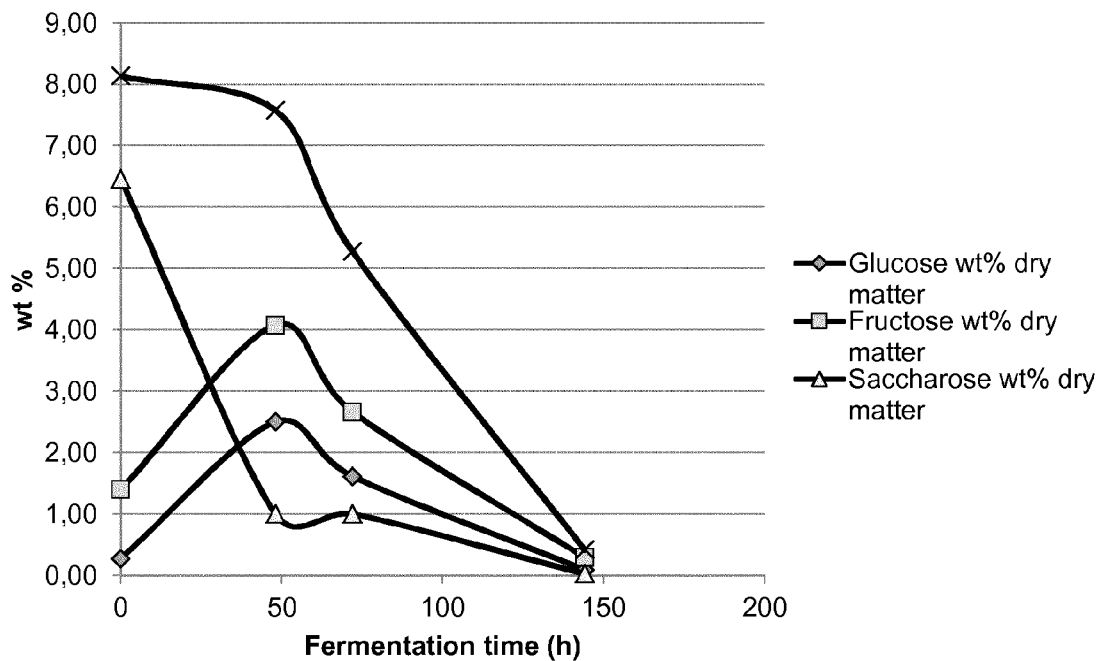
FIG. 34: represents a graph plotting the evolution of free sugars concentration over time at 30° C. of composition F incubated with *Saccharomyces bayanus* var. *uvarum* MUCL 55125. Analyses were performed using HPAEC-PAD (results expressed as wt/wt %).

FIG. 34 shows the evolution of free sugars concentration over time at 30° C. of composition F incubated with *Saccharomyces bayanus* var. *uvarum* MUCL 55125 in a 60 L barrel. Analyses were performed using HPAEC-PAD (results expressed as wt/wt % based on the total dry matter basis).

Figure 35:
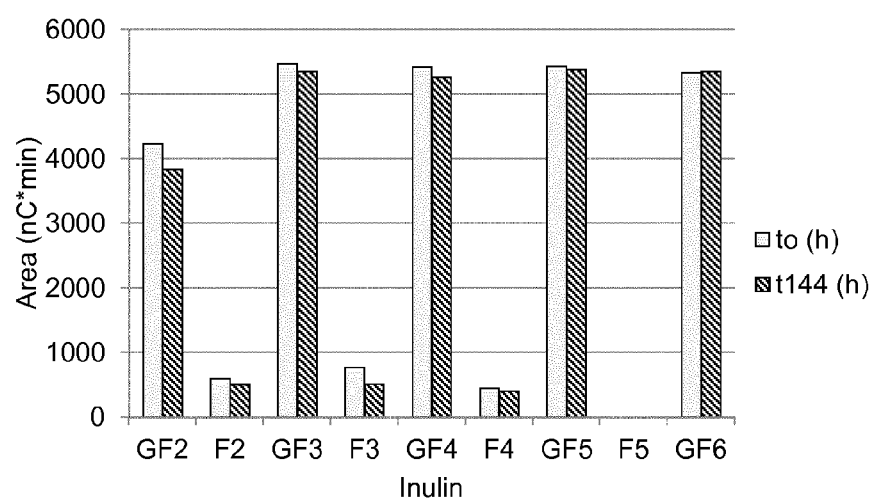
FIG. 35: represents a graph plotting the evolution of peak area of GF2, F2, GF3, F3, GF4, F4, GF5, F5 and GF6 over time at 30° C. of composition F incubated with *Saccharomyces bayanus* var. *uvarum* MUCL 55125. Analyses were performed using HPAEC-PAD (with the area given in nanocoulomb (nC)*retention time (min)—normalized according to the dilution of the composition).

FIG. 35 shows the evolution of peak area of GF2, F2, GF3, F3, GF4, F4, GF5, F5 and GF6 over time at 30° C. of composition F incubated with *Saccharomyces bayanus* var. *uvarum* MUCL 55125 in a 60 L barrel. Analyses were performed using HPAEC-PAD (with the area given in nanocoulomb (nC)*retention time (min)–normalized according to the dilution of the composition).

Example 9

Specificity of *Kluyveromyces lactis* CBS 2103 for a Composition Comprising Inulin, Sucrose and Other Free Sugars—Step (b)

A yeast extract solution was prepared as follows: 20 g of yeast extract (Merck) were dissolved in 200 ml of demineralized water and sterilized (20 min, 121° C.).

200 g of the sterilized yeast extract solution was added in 2 L bioreactor containing 1800 g of the composition C.

No supplemental aeration was provided. pH of the composition was maintained at a value of 5 using a peristaltic pump providing basic solution as sodium hydroxide 10 mol/L and acid solution as phosphoric acid 30 vol/vol %.

Composition C, complemented with yeast extract, was incubated at a concentration of $10^5$ CFU/ml at 20° C. under a stirring rate of 160 rpm with *Kluyveromyces lactis* CBS 2103 (from CBS-KNAW fungal biodiversity center, Utrecht NL).

Figure 36:
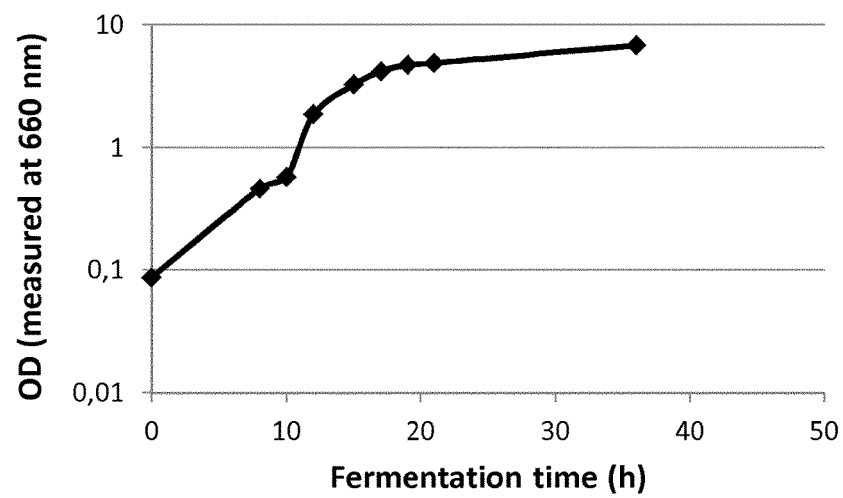
FIG. 36: represents a graph plotting the growth (measured as optical density at 660 nm) over time at 20° C. of *Kluyveromyces lactis* CBS 2103 incubated with composition C.

FIG. 36 shows the growth (measured as optical density) over time at 20° C. of *Kluyveromyces lactis* CBS 2103 incubated with composition C in a 2 L bioreactor.

Figure 37:
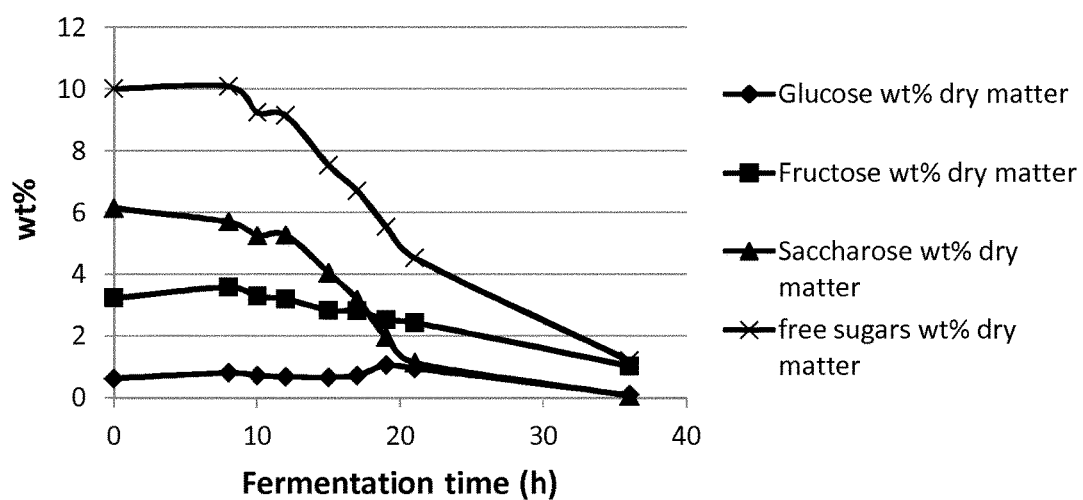
FIG. 37: represents a graph plotting the evolution of free sugars concentration over time at 20° C. of composition C incubated with *Kluyveromyces lactis* (CBS 2103). Analyses were performed using HPAEC-PAD (results expressed as wt/wt % based on the total dry matter basis).

FIG. 37 shows the evolution of free sugars concentration over time at 20° C. of composition C incubated with *Kluyveromyces lactis* CBS 2103 in a 2 L bioreactor. Analyses were performed using HPAEC-PAD (results expressed as wt/wt % based on the total dry matter basis).

Figure 38:
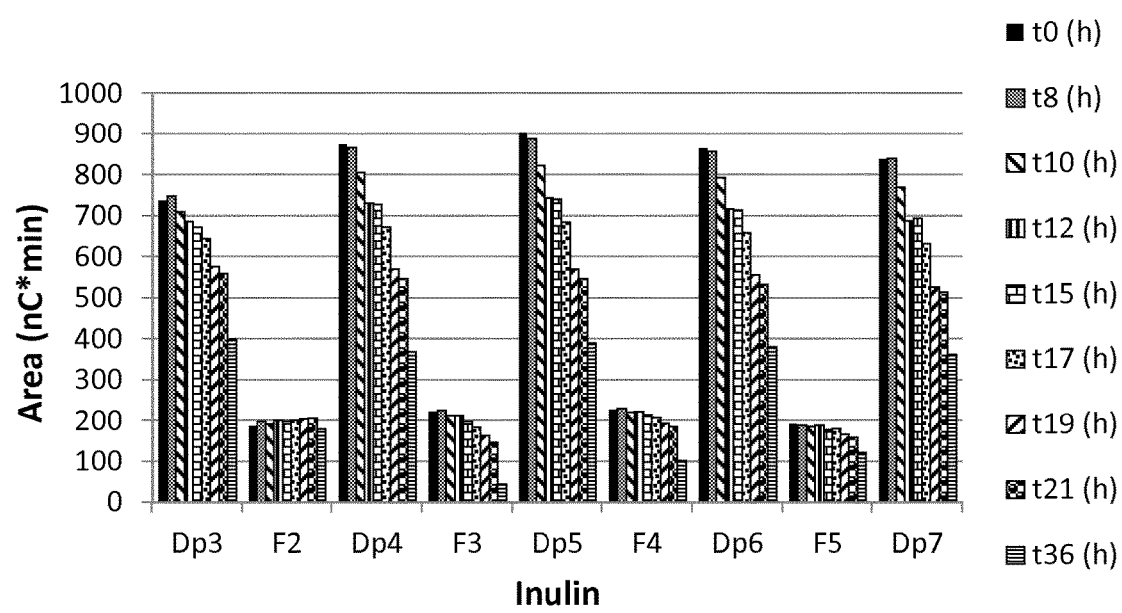
FIG. 38: represents a graph plotting the evolution of peak area of GF2, F2, GF3, F3, GF4, F4, GF5, F5 and GF6 over time at 20° C. of composition C incubated with *Kluyveromyces lactis* (CBS 2103). Analyses were performed using HPAEC-PAD (with the area given in nanocoulomb (nC) *retention time (min)—normalized according to the dilution of the composition).

FIG. 38 shows the evolution of peak area of GF2, F2, GF3, F3, GF4, F4, GF5, F5 and GF6 over time at 20° C. of composition C incubated with *Kluyveromyces lactis* CBS 2103 in a 2 L bioreactor. Analyses were performed using HPAEC-PAD (with the area given in nanocoulomb (nC)*retention time (min)—normalized according to the dilution of the composition).

The invention claimed is:

1. A method for processing a composition comprising fructan and sucrose, comprising the steps of (a) providing a composition comprising fructan and sucrose, wherein said composition comprising fructan and sucrose comprises at least 30% by weight (wt %) of fructan based on the total dry matter weight of said composition; and (b) incubating said composition comprising fructan and sucrose with at least one yeast selected from the group consisting of *Saccharomyces* and *Kluyveromyces*; until a reduction of at least 10% of the initial weight of sucrose in said composition is obtained and wherein at the end of step (b) the fructan weight is at most 20% lower than the initial fructan weight.

2. The method according to claim 1, wherein said at least one yeast is selected from the group consisting of *Saccharomyces bayanus, Kluyveromyces lactis, Saccharomyces cerevisiae*, and *Saccharomyces boulardii*.

3. The method according to claim 1, wherein said fructan has an average degree of polymerization by number of at least 3.

4. The method according to claim 1, wherein said fructan is of plant origin.

5. The method according to claim 1, wherein said fructan is inulin.

6. The method according to claim 1, wherein said yeast is *Saccharomyces bayanus* var. *uvarum* deposited in the Belgian Co-ordinated Collections of Micro-Organisms (BCCM) with accession number MUCL 55125.

7. The method according to claim 1, wherein said composition comprising fructan and sucrose is incubated with said yeast at a temperature of at least the freezing point of the composition.

8. The method according to claim 1, wherein said composition comprising fructan and sucrose is incubated with said yeast at a pH of at least 2.5.

9. The method according to claim 1, wherein said composition comprising fructan and sucrose comprises at least 5 wt % and at most 80 wt % of dry matter based on the total weight of the composition.

10. A composition comprising fructan, sucrose and at least one yeast selected from the group consisting of *Saccharomyces bayanus, Saccharomyces cerevisiae, Kluyveromyces lactis*, and *Saccharomyces boulardii*, wherein said composition comprises at least 30% by weight (wt %) of fructan based on the total dry matter weight of said composition.

11. A yeast deposited in the Belgian Co-ordinated Collections of Micro-Organisms (BCCM) with accession number MUCL 55125, wherein the yeast is *Saccharomyces bayanus var. uvarum*.

12. The method according to claim 4, wherein said fructan is of chicory origin.

13. The method according to claim 5, wherein said fructan is chicory inulin.

14. The method according to claim 1, wherein at the end of said incubating step the fructan weight of said composition comprising fructan and sucrose is at most 10% lower than the initial fructan weight.

15. The method according to claim 1, wherein at the end of said incubating step the fructan weight of said composition comprising fructan and sucrose is at most 5% lower than the initial fructan weight.

* * * * *